US008910212B2

(12) United States Patent
Harris et al.

(10) Patent No.: US 8,910,212 B2
(45) Date of Patent: Dec. 9, 2014

(54) MULTIPLE DEVICE STOREFRONT FOR VIDEO PROVISIONING SYSTEM

(75) Inventors: Jeffery Lionel Harris, Leesburg, VA (US); John K. Trimper, Groton, MA (US)

(73) Assignee: Verizon Patent and Licensing Inc., Basking Ridge, NJ (US)

(*) Notice: Subject to any disclaimer, the term of this patent is extended or adjusted under 35 U.S.C. 154(b) by 487 days.

(21) Appl. No.: 13/196,286

(22) Filed: Aug. 2, 2011

(65) Prior Publication Data

US 2012/0079529 A1    Mar. 29, 2012

Related U.S. Application Data

(60) Provisional application No. 61/387,939, filed on Sep. 29, 2010.

(51) Int. Cl.
*H04N 5/445* (2011.01)
*H04N 7/173* (2011.01)
*G06F 17/30* (2006.01)
*H04N 21/431* (2011.01)
*H04N 21/475* (2011.01)
*H04N 21/84* (2011.01)
*H04N 21/2225* (2011.01)
*H04N 21/8549* (2011.01)
*H04N 21/2668* (2011.01)
*A61N 5/06* (2006.01)
*H04N 21/472* (2011.01)
*H04N 21/258* (2011.01)

(52) U.S. Cl.
CPC .......... *A61N 5/0618* (2013.01); *H04N 21/4316* (2013.01); *H04N 21/4755* (2013.01); *H04N 21/84* (2013.01); *H04N 21/2225* (2013.01); *H04N 21/8549* (2013.01); *H04N 21/2668* (2013.01); *H04N 21/47202* (2013.01); *H04N 21/25891* (2013.01)
USPC .................................. 725/46; 725/58; 725/80

(58) Field of Classification Search
CPC ................... H04N 21/47217; H04N 21/4821; H04N 21/25825; H04N 21/25833
USPC ........................................ 725/46, 48, 80, 58
See application file for complete search history.

(56) References Cited

U.S. PATENT DOCUMENTS

| | | | | |
|---|---|---|---|---|
| 6,470,378 | B1* | 10/2002 | Tracton et al. | 709/203 |
| 2006/0215650 | A1* | 9/2006 | Wollmershauser et al. | 370/389 |
| 2007/0113246 | A1* | 5/2007 | Xiong | 725/39 |
| 2007/0157260 | A1* | 7/2007 | Walker | 725/86 |
| 2008/0092184 | A1* | 4/2008 | Kim et al. | 725/110 |
| 2008/0301732 | A1* | 12/2008 | Archer et al. | 725/40 |
| 2009/0112808 | A1* | 4/2009 | Howcroft et al. | 707/3 |
| 2010/0281506 | A1* | 11/2010 | Schmidt et al. | 725/46 |
| 2011/0138432 | A1* | 6/2011 | Mitra et al. | 725/109 |

(Continued)

*Primary Examiner* — Benjamin R Bruckart
*Assistant Examiner* — Carmine Malangone

(57) ABSTRACT

A system may process metadata associated with video assets; generate, based on the metadata, a first listing of the video assets, where the first listing is compatible with a first type of user device that corresponds to a set top box; and provide the first listing to the first type of user device. The system may further generate, based on the metadata, a second listing of the video assets, where the second listing is formatted to be compatible with a second type of user device that is a different type than the set top box; and provide the second listing to the second type of user device.

24 Claims, 15 Drawing Sheets

(56) References Cited

U.S. PATENT DOCUMENTS

2011/0258665 A1\* 10/2011 Fahrny et al. ............... 725/47
2012/0017245 A1\* 1/2012 Chen et al. ............... 725/54
2013/0167168 A1\* 6/2013 Ellis et al. ............... 725/12

\* cited by examiner

| ASSET ID 405 | TITLE 410 | GENRE 415 |
|---|---|---|
| DESCRIPTION 420 | CAST INFO 425 | RATING 430 |
| PRICE 435 | FORMAT 440 | CATEGORY 445 |
| REVIEWS 450 | COVER ART 455 | BUNDLE 460 |

400

FIG. 4

MULTIPLE DEVICE STOREFRONT FOR VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND

Users, of user devices, have a growing array of sources, networks, and/or content providers from which to obtain video content and/or services. The users may use video client devices (e.g., a set top box ("STB"), etc.) to obtain free broadcast television video content (e.g., from Fox, ABC, CBS, etc.), on-demand video content (e.g., Video On-Demand (VOD), pay-per-view (PPV), etc.), and/or pay television video content (e.g., from HBO, Cinemax, etc.) from cable television operators (e.g., Comcast, Time Warner, etc.) and/or satellite television operators (e.g., DirectTV, Dish Network, etc.). The users may use computer devices, wireless mobile handset devices, etc. to obtain other video content from on-line content providers, such as television operators (e.g., ABC, Fox, CBS, etc.), over-the-top (OTT) content providers (e.g., Hulu, Veoh, Jaman, YouTube, etc.), and/or other commercial content providers (e.g., Apple Computer's iTunes, Netflix, Blockbuster, etc.).

BRIEF DESCRIPTION OF THE DRAWINGS

FIG. 4 is a schematic diagram of an example data structure that stores metadata associated with a video asset according to an implementation described herein;

DETAILED DESCRIPTION OF PREFERRED EMBODIMENTS

The following detailed description refers to the accompanying drawings. The same reference numbers in different drawings may identify the same or similar elements.

The systems and/or methods may permit a user to register various different types of user devices (e.g., desktop computers, laptop computers, and tablet computers), wireless devices (e.g., mobile phones, smart phones, personal digital assistants (PDAs), and tablet computers), gaming devices, and/or STBs, to define storefront configuration criteria for the different types of user devices, and to associate the various different types of user devices with the user's account.

The systems and/or methods may enable different types of registered user devices to access metadata associated with video assets via a storefront associated with a video provisioning system (VPS). The metadata may describe the video asset and/or may enable the video asset to be processed, managed, offered to the user device, and/or provisioned, by the VPS, to the user device. The storefront may, for example, be an interactive media guide (IMG) (e.g., for STBs), a user interface, a webpage etc. via which the different types of user devices may access, browse, search, and/or select metadata associated with video assets.

The systems and/or methods may permit the metadata to be sent to a user device, which allows a user, of the user device, to read a description of the video asset, view cover art associated with the video asset, read reviews associated with the video asset, etc. The systems and/or methods may allow the user device to identify whether a video asset is compatible with that user device or with another user device associated with the user. The systems and/or methods may allow the user device to purchase, rent, or subscribe to the video asset, which may cause the VPS to automatically transmit the video asset, to the user device, or may cause the VPS to provide a location of the video asset for access by the user device.

Figure 1:
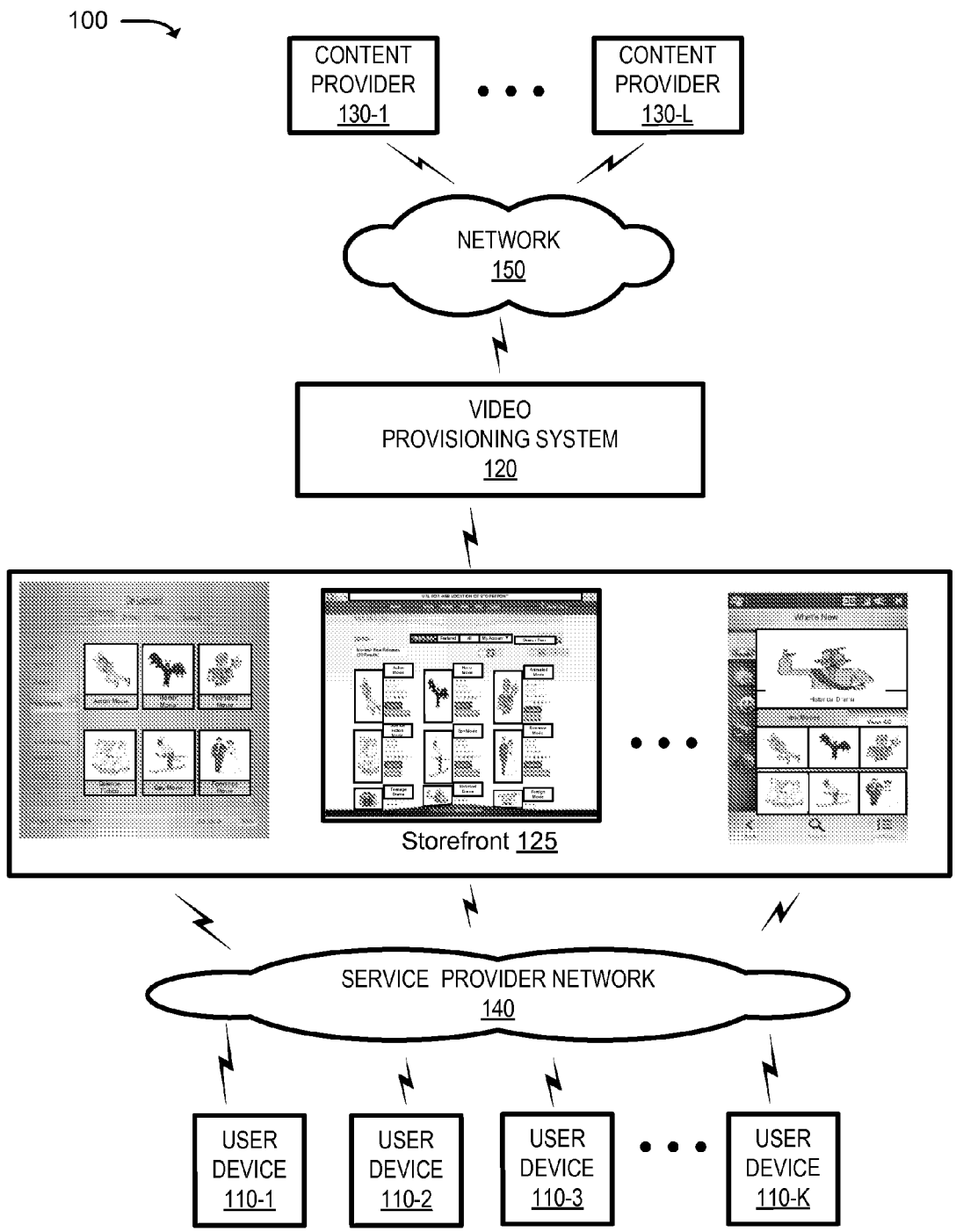
FIG. 1 is a diagram of an example environment in which the systems and/or methods, described herein, may be implemented.

FIG. 1 is a diagram of an example environment 100 in which the systems and/or methods, described herein, may be implemented. As shown in FIG. 1, environment 100 may include a group of user devices 110-1, . . . , 110-J (where K≥1) (hereinafter referred to collectively as "user devices 110" and individually as "user device 110"), a video provisioning system (VPS) 120, a group of content providers 130-1, . . . , 130-L (where L≥1) (hereinafter referred to collectively as "content providers 130" and individually as "content provider 130"), a service provider network 140, and a network 150. The number of devices, systems, and/or networks, illustrated in FIG. 1, is provided for explanatory purposes only. In practice, there may be additional devices, systems, and/or networks; fewer devices, systems, and/or networks; different devices, systems, and/or networks; or differently arranged devices, systems, and/or networks than illustrated in FIG. 1.

Also, in some implementations, one or more of the devices of environment 100 may perform one or more functions described as being performed by another one or more of the devices of environment 100. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a STB, a digital video recorder (DVR), a personal gaming system, a smart phone, or another type of computation or communication device.

User device 110 may communicate with VPS 120 and/or perform certain operations to obtain a video asset from VPS 120. For example, user device 110 may interact with VPS 120 to browse, search, select, and/or obtain a video asset.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. VPS 120 may communicate with one or more content providers 130 to acquire video content. VPS 120 may connect to a collection of different types of user devices 110 associated with a user, such as, for example, a STB, a computer device, a wireless device, and/or other types of user devices 110. VPS 120 may connect to the STB via a television service provider network 140 (e.g., a cable television network, a satellite television network, a fiber optic television network, or some combination thereof). VPS 120 may connect to the computer device via a broadband service provider network 140 (e.g., via the Internet). VPS 120 may connect to the wireless device 110 via a wireless service provider network 140. VPS 120 may perform an ingestion operation on the acquired video content. VPS 120 may process and/or publish the ingested video content in a manner that allows the video content to be offered and/or distributed to the different types of user devices 110.

As shown in FIG. 1, VPS 120 may provide differently formatted versions of a storefront 125. Storefront 125 may be a portal (e.g., a website, a user interface, an interactive program guide (IPG), an interactive media guide (IMG), etc.) that allows users, through user devices 110, to browse, search, select, and/or obtain a video asset. Storefront 125 may present the same content, related to the video assets, in different formats. The formats used for storefront 125 may be configured, respectively, for different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.). Content provider 130 may include on-demand content providers (e.g., video on demand (VOD), pay per view (PPV), etc.). A media stream, as used herein, may refer to a stream of content that includes video content (e.g., a video stream), audio content (e.g., an audio stream), and/or textual content (e.g., a textual stream).

The term video asset, as used herein, may include VOD content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

Content provider 130 may provide metadata associated with video assets. The metadata may describe the video asset and/or may enable the video asset to be processed, stored, managed, offered, and/or distributed to user device 110. Content provider 130 may, in another example, provide metadata, associated with video assets that are not yet available for distribution to user devices 110. The metadata may identify a date when the video assets can be made available and/or distributed to user devices 110.

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Figure 2:
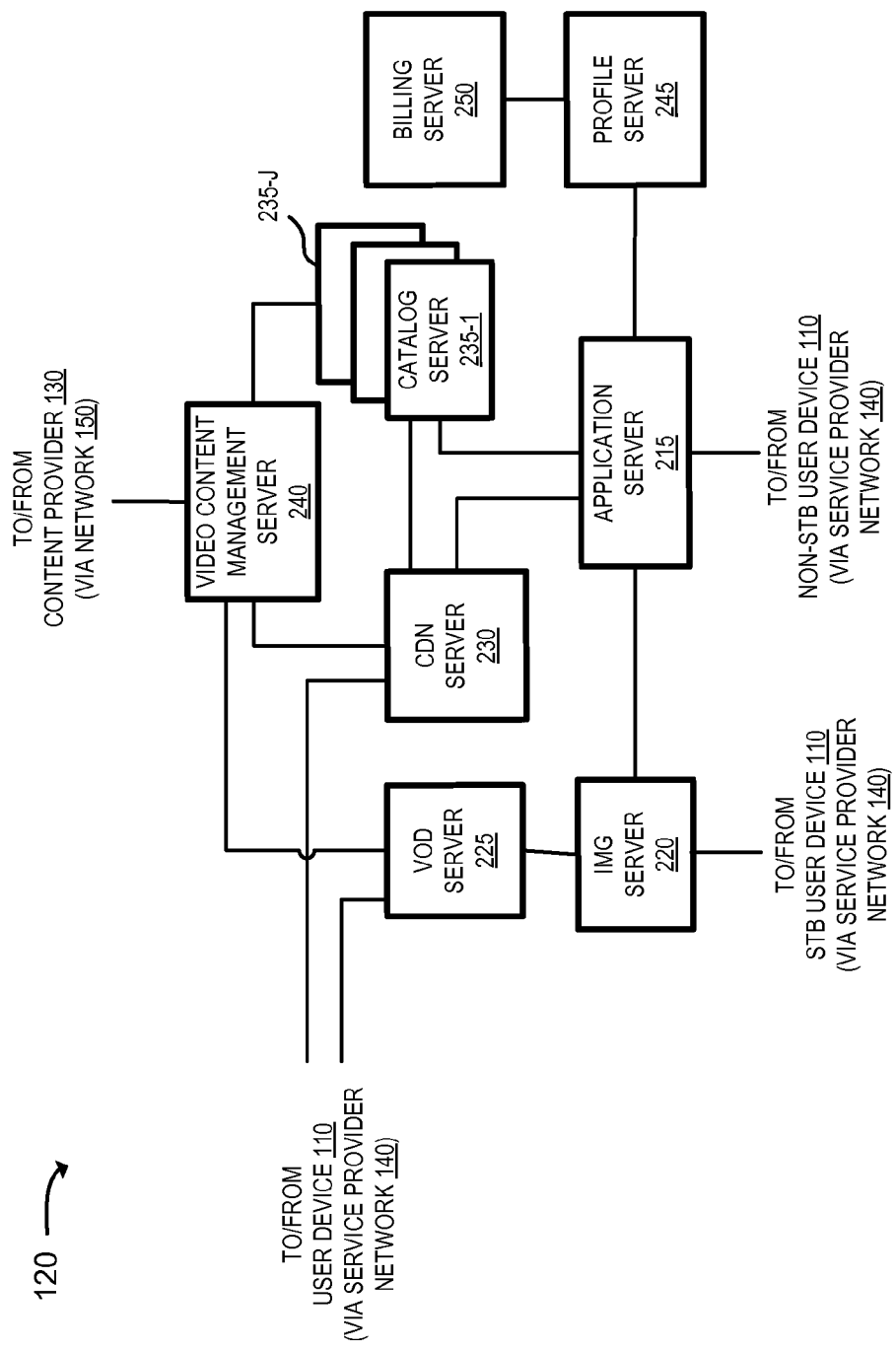
FIG. 2 is a diagram of example devices, associated with a video provisioning system included in the environment of FIG. 1.

FIG. 2 is a diagram of example devices associated with VPS 120. VPS 120 may include an application server 215, an interactive media guide (IMG) server 220, a video on-demand (VOD) server 225, a content delivery network (CDN) server 230, a group of catalog servers 235-1, . . . , 235-J (where J≥1) (hereinafter referred to collectively as "catalog servers 235" and individually as a "catalog server 235"), a video content management (VCM) server 240, a profile server 245, and a billing server 250. The number of devices illustrated in FIG. 2 is provided for explanatory purposes only. In practice, there may be additional devices; fewer devices; or differently arranged devices than illustrated in FIG. 2. Additionally, or alternatively, one or more devices of VPS 120 may perform one or more tasks described as being performed by one or more other devices of VPS 120.

In the description below, VOD server 225 is described as provisioning video services for a type of user device 110 (i.e., a STB) and CDN server 230 is described as provisioning video services for another type of user device 110 (i.e., a computer device, a wireless handset device, etc.) for explanatory purposes. In another implementation, the video services may be provisioned for the STB and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230.

Additionally, IMG server 220 is described as providing one type of storefront 125 (i.e., via an IMG), which can be accessed by the STB, and application server 215 is described as providing another type of storefront 125 (e.g., via a web page, a user interface, an interactive program guide, etc.), that can be accessed by the other types of user devices 110, for explanatory purposes. In another implementation, storefront 125 may be provisioned for the STB and/or the other types of user devices 110 in a number of ways. For example, IMG server 220 and/or application server 215 may be combined into a single device that provisions storefront 125 for each type of user device 110. In another example, storefront 125 may be provisioned, for each type of user device 110, by another device and/or network instead of, or in combination with, IMG server 220 and/or application server 215. Thus, the examples below are provided for explanatory purposes only.

Application server 215 may include one or more server devices, or other types of computation or communication devices, that gather, process, search, store, and/or provide information in a manner similar to that described herein. Application server 215 may receive metadata that has been published by catalog server 235. The metadata may, in one example, be associated with video assets that are stored in CDN server 230 or another device.

Application server 215 may host storefront 125, such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for STB type user devices 110) and/or other types of user interfaces. Application server 215, when hosting storefront 125, may publish all or a portion of the metadata, associated with the video assets, to storefront 125 to permit user device 110 to browse, perform searches, process payment, etc. for video assets based on the metadata that is published to storefront 125. Application server 215 may provide storefront 125 to enable single sign-on (SSO) portal access, by the user of one or more user devices 110, based on the similar login credentials (e.g., username, password, personal identification number (PIN), etc.).

Application server 215 may store information associated with a transaction history associated with the user. Application server 215 may store a transaction history that specifically corresponds to a type of user device 110 (e.g., a computer user device 110, a wireless handheld user device 110, a gaming user device 110, etc.) that is different than STB type user device 110. The transaction history may include information regarding prior transactions (e.g., purchases, rentals, subscriptions, etc.), associated with one or more video assets by user device 110. The transaction history may also identify a period of time during which a rental period or subscription period, for a video asset, is valid to be distributed to user device 110. Application server 215 may transmit information, associated with the transaction history, to profile server 245, to be stored in a profile associated with the user of user device 110.

IMG server 220 may include one or more server devices, or other types of computation or communication devices, that gather, process, search, store, and/or provide information in a manner similar to that described herein. IMG server 220 may, for example, publish storefront 125 via an IMG that displays metadata associated with the video assets, and an STB type user device 110, associated with the user, may render the IMG for display on an associated video display device. IMG server 220 may permit STB type user device 110 to access, through storefront 125, information associated with video assets that stored by VOD server 225.

IMG server 220 may, as part of publishing storefront 125, process metadata, that has been published by catalog server 235 and/or VOD server 225, in a manner similar to that described above (e.g., with respect to application server 215). The metadata may be associated with video assets that are stored in VOD server 225. The metadata may be accessed and/or obtained through storefront 125, via IMG server 220, by a particular type of user device 110, such as STB type user device 110.

IMG server 220 may permit user device 110 to access a user's transaction history. IMG server 220 may store information associated with the user's transaction history that corresponds to STB type user device 110. IMG server 220 may publish, through storefront 125, all or a portion of the user's transaction history. The transaction history may include information regarding prior transactions (e.g., purchases, rentals, subscriptions, etc.), associated with one or more video assets by STB type user device 110. The transaction history may also identify a period of time during which a rental period or subscription period, for a video asset, is valid. The transaction history may identify when a video asset that has been purchased, rented, or subscribed and/or is distributed to user device 110. IMG server 220 may, in another example, transmit information, associated with the transaction history, to profile server 245, to be stored in a profile associated with a user of user device 110.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by user device 110, such as an STB.

VOD server 225 may receive published video assets and/or metadata from VCM server 240. VOD server 225 may store the published video assets in a memory associated with VOD server 225. VOD server 225 may publish the metadata, associated with video assets, to IMG server 220 to be provided through storefront 125. In another example implementation, VOD server 225 may communicate with content provider 130 to receive video content directly from content provider 130 (e.g., not via VCM server 240).

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, STB type user device 110. CDN server 230 may represent a content delivery network that includes multiple routing and/or storage devices.

CDN server 230 may receive published video assets in one or more video formats from VCM server 240. CDN server 230 may store the published video assets in a memory associated with CDN server 230. CDN server 230 may identify a respective storage location and/or URL for each format of each video asset that is stored within the memory and may send information associated with the storage locations and/or the URLs to catalog server 235. CDN server 230 may provide video assets to wireless handset user devices 110 via a wireless service provider network 140. CDN server 230 may provide the video assets to a computer user device 110 via a broadband service provider network 140 (e.g., the Internet). In another example implementation, CDN server 230 may provide the video assets to STB type user device 110 via a television service provider network 140 and/or via VOD server 225.

Catalog server 235 may include one or more server devices, or other types of computation or communication devices, that gather, process, search, store, and/or provide information in a manner similar to that described herein. Catalog server 235 may, for example, receive, from VCM server 240, published metadata associated with video assets that have been published to VOD server 225 and/or CDN server 230. Catalog server 235 may identify, from the metadata, information associated with the availability of the video assets based on dates on which the video assets are released, blacked out, etc. Catalog server 235 may process and/or package the metadata in order to offer, through storefront 125, the video assets to which the metadata corresponds. Catalog server 235 may process and/or package the other metadata to create a video asset that can be offered, through storefront 125, to user devices 110. The processed metadata associated with the video assets may include identifiers (e.g., video asset numbers, titles, etc.), availability dates, prices (e.g., sale prices, rental prices, subscription prices, etc.), cover art (e.g., images, trailers, etc.), descriptions (e.g., a synopsis, a summary, etc. of the video assets), ratings, reviews, genres, casting information (e.g., actors, directors, producers, etc.), etc. Catalog server 235 may, for example, forward the metadata to application server 215 to be provided through storefront 125.

Different catalog servers 235 may be associated with different content providers 130. Additionally, or alternatively, different catalog servers 235 may be associated with different types of user device 110.

VCM server 240 may include one or more server devices, or other types of computation or communication devices, that gather, process, search, store, and/or provide information in a manner similar to that described herein. VCM server 240 may, for example, communicate with content providers 130 to ingest video assets to be processed by VPS 120. VCM server 240 may process the video assets to generate copies of the video assets in one or more formats that are supported (e.g., that can be received, processed, and/or played) by the different types of user devices 210. VCM server 240 may publish the one or more formats, associated with the processed video assets, to VOD server 225 and/or CDN server 230.

VCM server 240 may also ingest, process, and/or publish metadata associated with the video assets. VCM server 240 may process the metadata to ensure that the metadata is compatible, via storefront 125, for the different types of user devices 210. VCM server 240 may publish the processed metadata to catalog server 235 and/or VOD server 225 for inclusion in storefront 125.

Profile server 245 may include one or more server devices, or other types of computation or communication devices, that gather, process, search, store, and/or provide information in a manner similar to that described herein. Profile server 245 may, for example, store information associated with a profile that includes information regarding the user and/or each user device 110 that the user has registered with VPS 120. For example, information associated with the profile may further include information associated with the user (e.g., a username, password, PIN, etc.), information associated with each user device 110, such as a respective identifier (e.g., a mobile directory number (MDN), an Internet protocol (IP) address, a media access control (MAC) address, a compression/decompression (CODEC) identifier, etc.), and/or information associated with types of user devices 110, such as a computer device (e.g., a lap top computer, a tablet computer, etc.), a wireless mobile device (e.g., a Droid®, a Blackberry®, an iPhone®, etc.), an STB, a gaming device, etc.

Profile server 245 may store information, associated with the profile, that includes a respective transaction history (e.g., prior purchases, rentals, and/or subscriptions; prior URLs accessed; prior downloads; etc.) associated with each user device 110; information associated with services for which user device 110 has subscribed; information associated with a location (e.g., an address, a zip code, a city, etc.) of the user and/or user device 110; information associated user account limits, restrictions, etc.; information associated with a language spoken by the user; etc. Profile server 245 may communicate with application server 215 to obtain a first transaction history, associated with user device 110, that are different types of user devices 110 than STB type user device 110, such as a computer user device 110, a wireless handheld user device 110, a gaming user device 110, etc. Profile server 245 may communicate with IMG server 220 to obtain a second transaction history, associated with STB type user device 110. Profile server 245 may store information obtained from the first transaction history and/or the second transaction history in a profile associated with a user of STB type user device 110 and/or non-STB type user device 110.

Profile server 245 may communicate with application server 215 and/or IMG server 220 to provide user device 110 with access, via storefront 125, to one or more transactions histories associated with the user. A user may view through, for example, a STB-type user device 110, the user's complete transaction history, including transactions conducted on the STB type user device 110 and transactions conducted on another non-STB type user device 110.

The information associated with the profile may include a bookmark that identifies metadata, associated with a video asset that has been selected by a user of user device 110. The bookmark may cause metadata, associated with a bookmarked video asset, to be stored in the profile to enable the user to access the bookmarked metadata within a period of time that is less than another period of time associated with obtaining the metadata (e.g., based on browsing, searching, etc.) via storefront 125 (e.g., application server 215 and/or IMG server 220).

Billing server 250 may include one or more server devices, or other types of computation or communication devices, that gather, process, search, store, and/or provide information in a manner similar to that described herein. Billing server 250 may, for example, perform billing operations associated with accounts that correspond to each user device 110 associated with a user. Billing server 250 may perform electronic transactions associated with purchasing, renting, subscribing to, etc. a video asset. When performing the electronic transaction, billing server 250 may process payment information associated with the electronic transaction.

Figure 3:
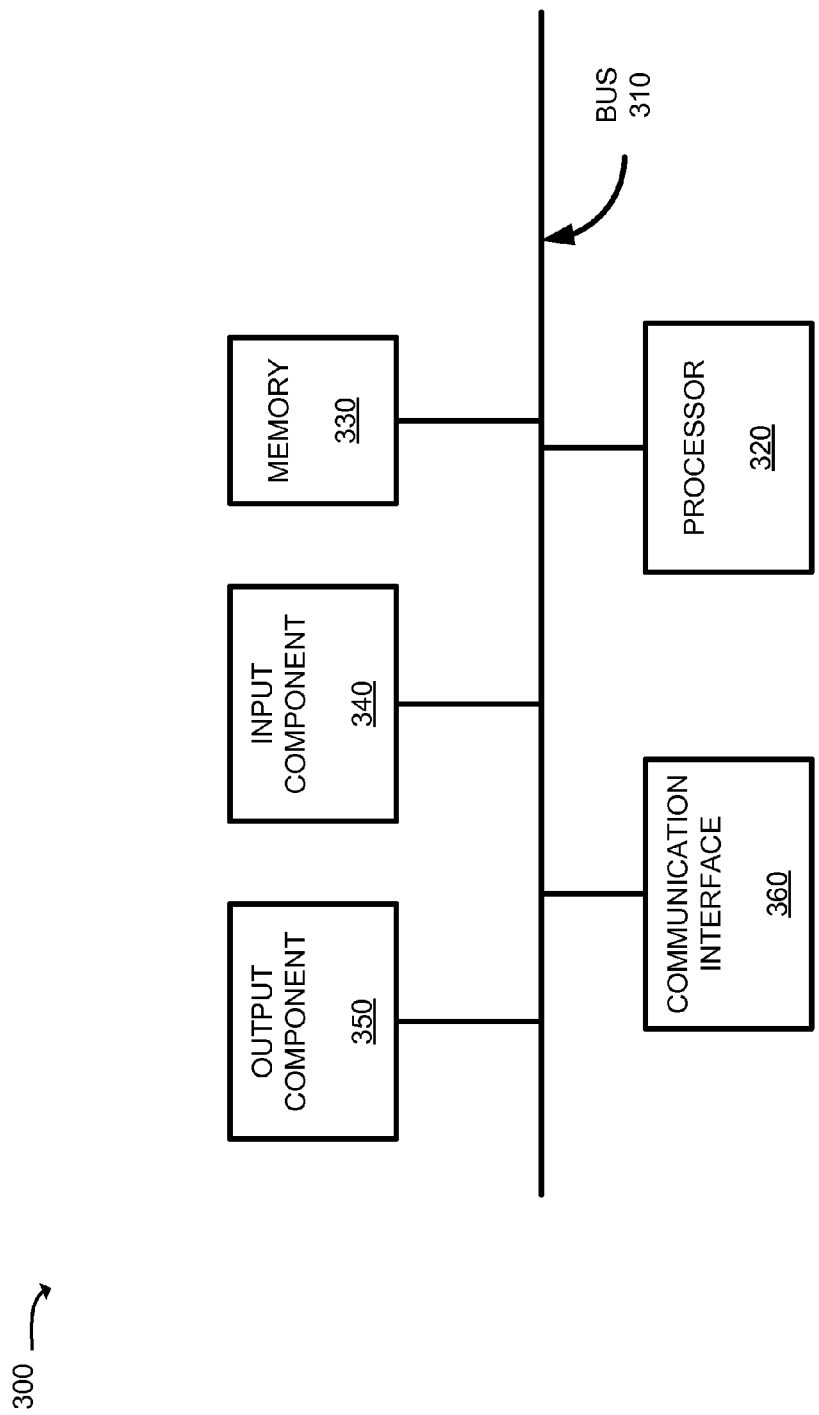
FIG. 3 is a schematic diagram of example components that correspond to one or more of the devices of FIGS. 2 and/or 3.

FIG. 3 is a diagram of example components of a device 300 that may correspond to user device 110, content provider 130, application server 215, IMG server 220, VOD server 225, CDN server 230, catalog server 235, VCM server 240, profile server 245, and/or billing server 250. Alternatively, each of user device 110, content provider 130, application server 215, IMG server 220, VOD server 225, CDN server 230, catalog server 235, VCM server 240, profile server 245, and/or billing server 250 may include one or more devices 300. Device 300 may include a bus 310, a processor 320, a memory 330, an input component 340, an output component 350, and a communication interface 360. Although FIG. 3 shows example components of device 300, in other implementations, device 300 may contain fewer components, additional components, different components, or differently arranged components than shown in FIG. 3. For example, device 300 may include one or more switch fabrics instead of, or in addition to, bus 310. Additionally, or alternatively, one or more components of device 300 may perform one or more tasks described as being performed by one or more other components of device 300.

Bus 310 may include a path that permits communication among the components of device 300. Processor 320 may include a processor, microprocessor, or processing logic that may interpret and execute instructions. Memory 330 may include any type of dynamic storage device that may store information and instructions, for execution by processor 320, and/or any type of non-volatile storage device that may store information for use by processor 320.

Input component 340 may include a mechanism that permits a user to input information to device 300, such as a keyboard, a keypad, a button, a switch, etc. Output component 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as service provider network 140 and/or network 150. In one alternative implementation, communication interface 360 may be a logical component that includes input and output ports, input and output systems, and/or other input and output components that facilitate the transmission of data to other devices.

As will be described in detail below, device 300 may perform certain operations relating to storefront 125 within video provisioning system 120. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

FIG. 4 is a diagram of an example data structure 400 that may store metadata associated with a video asset according to an implementation described herein. Catalog server 335 may store the metadata, published by VCM server 240, in data structure 400. Data structure 400 may include a collection of fields, such as asset identifier (ID) field 405, title field 410, genre field 415, description field 420, cast information (info) field 425, rating field 430, price field 435, format field 440, category field 445, reviews field 450, cover art field 455, and bundle field 460. Data structure 400 includes fields 405-460 for explanatory purposes. In practice, data structure 400 may include additional fields, fewer fields, different fields, or differently arranged fields than are described with respect to data structure 400.

Asset ID field 405 may store a unique identifier (e.g., one or more sequences of characters, etc.) associated with a particular video asset. Title field 410 may store a title associated with the particular video asset. Genre field 415 may store information associated with a genre that corresponds to the particular video asset. Description field 420 may store a description associated with the particular video asset, such as a summary of a movie, a television program, etc. Cast info field 425 may store information associated with an actor, a director, a producer, and/or other individuals associated with the particular video asset.

Rating field 430 may store information associated with a rating (e.g., general audience (G), parental guidance (PG), PG-13, restricted (R), mature audience (MA), etc.) that corresponds to the particular video asset. Price field 435 may store information, associated with one or more prices, that corresponds to the particular video asset. For example, one price may correspond to a sale price for the particular video asset. Another price may correspond to a rental price (e.g., a cost per viewing, per day, per week, etc.). One or more further prices may correspond to a price associated with a bundle of video assets and/or services that include the particular video asset.

Format field 440 may indicate one or more format attributes associated with a video asset, such as audio/visual attributes. Visual attributes identified in format field 440 may include, for example, a display resolution (e.g., standard or high definition) and/or display aspect ratio (e.g., a conventional 4:3 display ratio or a widescreen 16:9 display ratio). Audio attributes included in format field 440 may include for example, mono-channel audio, a two-channel stereo audio, and/or multiple channel surround sound audio. In addition, where a video asset associated with the asset ID, stored in asset ID field 405, is available in multiple formats, each of the multiple formats may separate associated with separate pricing information in price field 435. Format field may further include, for example, additional data regarding attributes about the format of video asset, such as an associated encoding algorithm and/or one or more available delivery methods, and/or Category field 445 may store information associated with a category that corresponds to the particular video asset. The information, associated with the category, may include, for example, an indication that the particular video asset corresponds to a movie, a television program, a video game, etc. Reviews field 450 may include information associated with reviews, by users associated with VPS 120 and possibly users not associated with VPS 120, of the particular video asset, such as reviews received from a third-party source or from other users.

Cover art field 455 may include one or more images associated with the particular asset. The one or more images may be associated with a scene, branding, a cast member, etc. associated with the video asset. Bundle field 460 may store information, associated with a bundle, that identifies other services, and/or video assets that are associated with the particular video asset. For example, bundle field 460 may store information associated with a package that is being offered, to user devices 110, at a discounted price. The package may include, for example, the particular video asset; promotional material associated with the package and/or other packages; and/or another video asset and/or service. The bundle may be associated with a price identified in price field 435.

Figure 5:
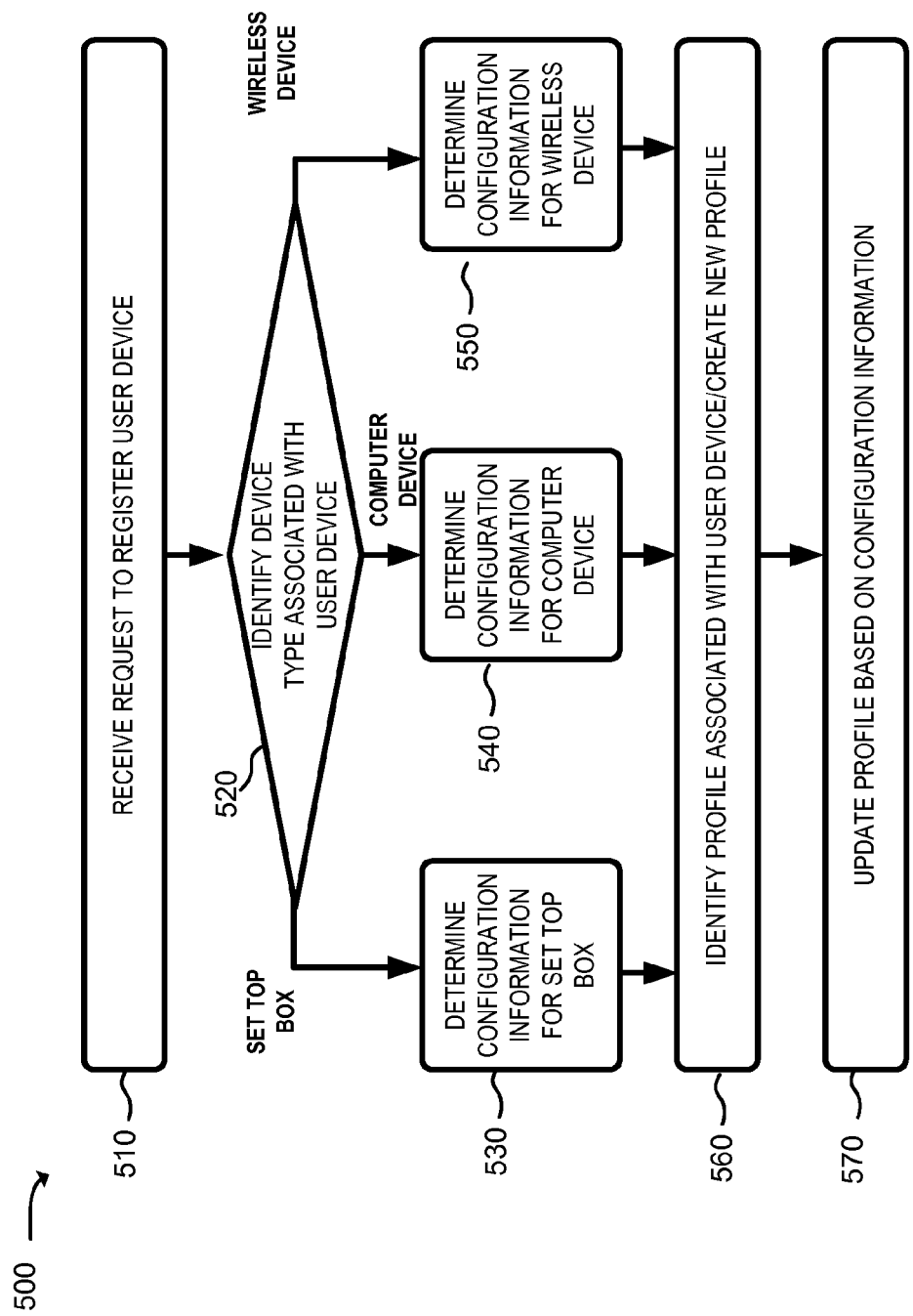
FIG. 5 is flowchart diagrams of an example process for registering a user device within the environment of FIG. 1.

FIG. 5 is a flowchart diagram of an example process 500 for registering a user device in connection with a video provisioning system. In one example implementation, process 500 may relate to registering user device 110 and may be performed by application server 215 and/or IMG server 220 in connection with profile server 245. In another example implementation, some or all of process 500 may be performed by a device, or collection of devices separate from, or in combination with application server 215, IMG server 220, and/or profile server 245.

Process 500 may include receiving a request to register a user device (block 510). For example, application server 215 and/or IMG server 220 may receive a registration request from user device 110. The registration request may include information associated with the user (e.g., username, password, PIN, etc.) and/or user device 110 (e.g., a device identifier, a network address, etc.). The registration request may be produced by an application, operating on user device 110, that collects information and/or prompts the user to provide information related to the registration of user device 110.

Process 500 may include identifying a device type associated with the user device (block 520). For example, application server 215 and/or IMG server 220 may identify a device type associated with user device 110 based on the information included in the registration request. Additionally, or alternatively, application server 215 and/or IMG server 220 may identify a device type associated with user device 110 based on information about service provider network 140 through which the registration request is received (e.g., a network identifier, a port and/or connection identifier, etc). For example, a registration request received through a television service provider network 140 may be associated with STB type user device 110; a registration request received through a broadband service provider network 140 (e.g., via the Internet) may be associated with a computer device type user device 110; and a registration request received through a wireless service provider network 140 may be associated with a wireless device type user device 110.

Process 500 may include, when the user device is an STB (block 520-Set Top Box), determining configuration information for the STB (block 530); when the user device is a computer device (block 520-computer device), determining configuration information for the computer device (block 540); and when the user device is a wireless device (block 520-wireless device), determining configuration information for the wireless device (block 550). For example, application server 215 and/or IMG server 220 may access configuration information for the identified type of user device 110 from profile server 245. The configuration information may be based on information included in the registration request. The configuration information may include device configuration information for user device 110 (e.g., compatible video formats, etc.) and/or user preferences (e.g., specifying one of the compatible video formats, types of transactions to include in a transaction history, a preferred time period for the transaction history, etc.). Profile server 245 may identify additional information about user device, such as an associated brand and/or model associated with user device 110, and profile server 245 may access configuration information associated user device based on this additional information. Additionally, or alternatively, application server 215 and/or IMG server 220 may acquire network configuration information for service provider network 140 associated with user device 110 (e.g., bandwidth limitations, compatible data formats, security protocols, etc.).

For example, a user may specify, in the registration request, that user device 110 should initially attempt to receive storefront 125 through a first service provider network 140, and then attempt to receive storefront 125 through a second service provider network 140 only when the first service provider network 140 is unavailable. Continuing with this example, the user may further specify, for example, that user device 110 should receive storefront 125 in a first format when accessed through the first service provider network 140 and in a second format when accessed through the second service provider network 140.

Process 500 may include identifying a profile associated with the user device (block 560). Profile server 245 may determine the user and/or user device 110 associated with the registration request and may identify a profile associated with the determined user and/or user device 110. Profile server 245 may determine the user and/or user device 110 based on the information included in the registration request. For example, profile server 245 may identify a profile based on information associated with the user (e.g., username, password, PIN, etc.) or information associated with user device 110 (e.g., a device identifier, a network address, etc.) that are included in the registration request.

In those situations where a profile cannot be identified (e.g., because no profile exists) for the user and/or user device 110, profile server 245 may create a new profile for the user and/or user device 110. The new profile may be based on the information included in the registration request. Additionally, or alternatively, storefront 125 may prompt the user to enter registration information. Once received, the registration information may be forwarded to profile server 245.

Process 500 may include updating the profile based on the configuration information (block 570). Profile server 245 may update the profile, identified in block 560, based on the configuration information for user device 110. The configuration information may be based on the information included in the registration request. For example, the configuration information may include user-specified device configuration information for user device 110 and/or user preferences related to configuration options for user device 110. Additionally, or alternatively, profile server 245 may update the profile based on the configuration information that is not included in the registration request, such as information about user device that is acquired from another source.

The profile may include a transaction history associated with the user, configuration information for user device 110, and/or user preferences. Updating the profile may include updating the transaction history associated with the profile. Updating the transaction history may include changing the transaction history to reflect transaction associated with user device 110. For example, the transaction history may be updated to include transactions that occurred prior to registration of user device 110 (e.g., transaction that are not associated with VPS 120).

While FIG. 5 shows a flowchart diagram of an example process 500 for registering a user device, in other implementations, process 500 may include fewer blocks, different blocks, differently arranged blocks, or additional blocks than depicted in FIG. 5.

Figure 6:
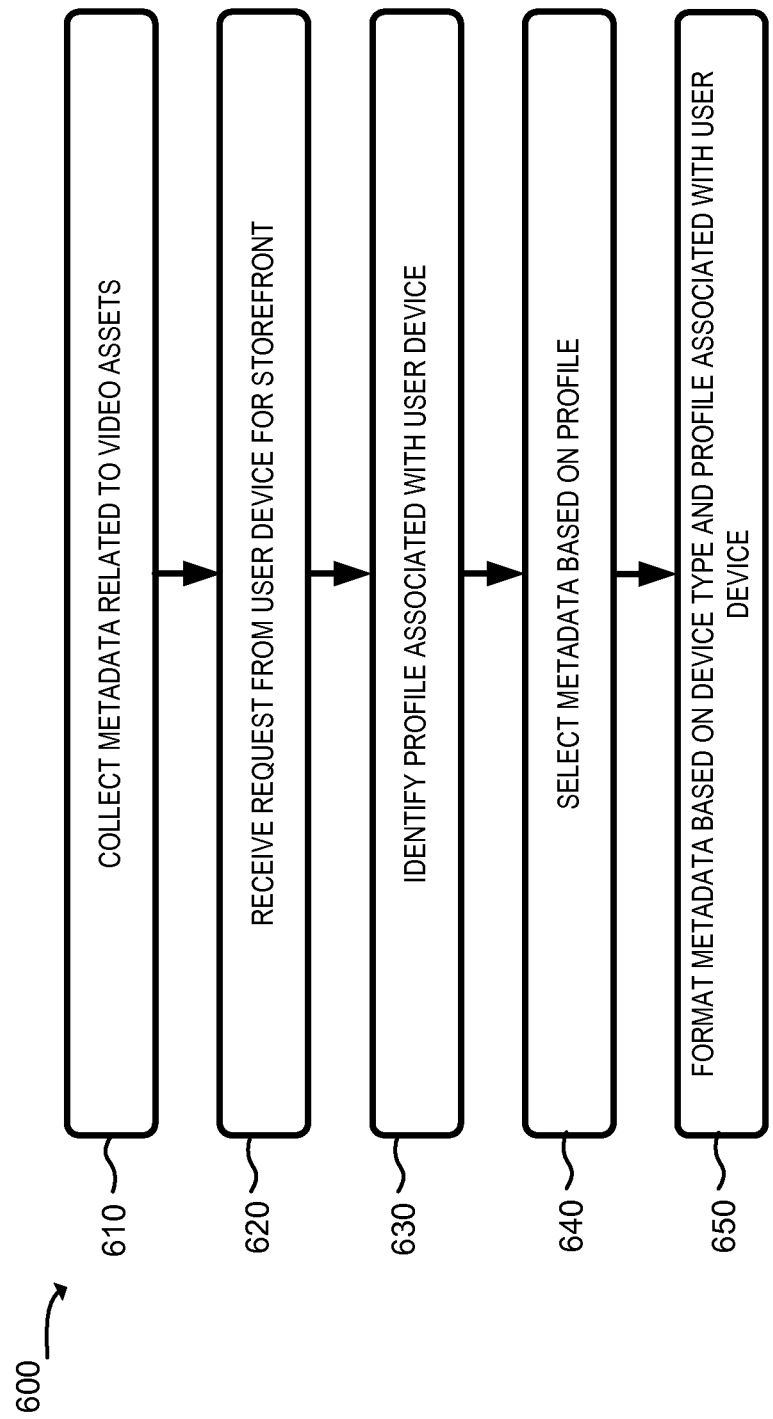
FIG. 6 is a flowchart diagram of an example process for forming a storefront within the environment of FIG. 1.

FIG. 6 is a flowchart diagram of an example process 600 for forming a storefront in connection with a video provisioning system. In one example implementation, process 600 may relate to forming storefront 125 and may be performed by application server 215 and/or IMG server 220, depending on a specific type of user device 110 requesting storefront 125. In another example implementation, some or all of process 600 may be performed by a device, or collection of devices separate from, or in combination with application server 215 and/or IMG server 220.

Process 600 may include collecting metadata related to video assets (block 610). For example, application server 215 and/or IMG server 220 may access, through VOD server 225 and/or CDN server 230, published metadata associated with video content that has been published to VOD server 225 and/or CDN server 230. Application server 215 and/or IMG server 220 may collect and store the metadata prior to receiving the request for the storefront or may collect the metadata in response to receiving the request. The collected metadata may correspond, for example, to one or more of the fields included in data structure 400 shown in FIG. 4.

Process 600 may include receiving a request from a user device for a storefront (block 620). For example, application server 215 and/or IMG server 220 may receive, from user device 110, a storefront request for storefront 125. The storefront request may include identifying information associated with the user (e.g., username, password, PIN, etc.) and/or user device 110 (e.g., a device identifier, a network address, a private key, a public key, a digital certificate, a confirmation number, etc.).

The storefront request may be sent in response to a user input through user device 110. For example, when user device 110 is an STB, the user may use a remote control to request a television channel associated with storefront 125. When user device 110 is not an STB, the user input may specify a uniform resource locator (URL) for a webpage associated with storefront 125, and the URL may enable user device 110 to access the webpage through a network, such as service provider network 140. In another implementation, the user input may activate an application, implemented through user device 110, to request storefront 125.

Process 600 may include identifying a profile associated with the user device sending the storefront request (block 630). For example, profile server 245 may identify a profile for the user. The profile may be identified through the information included in the storefront request (e.g., a storage location of the profile, an identifier for the user and/or user device 110, etc.) and/or through other information associated with the user and/or user device 110 (e.g., a network address on service provider network 140 associated with user device 110).

The profile identified in block 630 may identify a device type associated with the user device. For example, application server 215 and/or IMG server 220 may identify a device type associated with user device 110 based on the profile. The profile may indicate a device type associated with user device 110 based on information included in the storefront request. Additionally, or alternatively, application server 215 and/or IMG server 220 may identify the device type associated with user device 110 based on information about service provider network 140 through which the registration request is received.

Process 600 may include selecting metadata based on the profile (block 640). For example, application server 215 and/or IMG server 220 may select from the metadata collected in block 610. Application server 215 and/or IMG server 220 may select metadata according to user preferences included in the identified profile. For example, the selected metadata may be associated with one or more video assets identified through user preferences included in the profile (e.g., the user may specify particular video asset(s), one or more groups of video assets, and/or may specify criteria to select the video asset(s)). The selected metadata may be associated with a video asset that is identified based on a transaction history included in the profile (e.g., the user's prior purchases, rentals, subscriptions, and/or bookmarks). A video asset may be selected further based on information that is not included in the profile (e.g., promotional data associated with application server 215 and/or IMG server 220).

Additionally, or alternatively, application server 215 and/or IMG server 220 may select metadata associated with a group of video assets. Example groups may include newly released video assets (e.g., video assets that became available within a particular recent time period), what's popular (e.g., video assets that are more frequently purchased, rented, or subscribed to), a user-specified group (e.g., video assets that conform to one or more user-defined criteria), etc. A video asset may also be associated with one or more groups based on a category associated with video assets (e.g., whether the video asset is a movie, television show, etc.).

Application server 215 and/or IMG server 220 may select metadata based on the identified device type. For example, the user's profile may specify that storefront 125 initially present a particular video asset and/or group of video assets to one type of user device 110 and initially present another particular video asset and/or another group of video assets to another type of user device 110.

Process 600 may include formatting the metadata for the device type associated with user device 110 (block 650). For example, application server 215 and/or IMG server 220 may format the collected metadata based on the configuration information included in user profile. The configuration information in the user profile may identify, for example, a data format, an encryption technique, etc. supported by user device 110 and/or service provider network 140, and application server 215 and/or IMG server 220 may format the metadata based on the configuration information in the profile.

The information in the profile may further indicate different presentations of the selected metadata for different types of user device 110. For example, the information in the profile may specify an arrangement for the metadata (e.g., in a table, a scroll list, scroll bar, etc.) for each type of user device 110. Information in the profile may also specify how many video assets to concurrently present, via storefront 125, for each type of user device 110. The information in the profile may also specify different arrangements for metadata associated with different group of video assets. For example, application server 215 and/or IMG server 220 may arrange metadata associated with a group of video assets into a table, and format other metadata associated with another group of video assets into a scroll list.

Additionally, or alternatively, the selected metadata associated with one group of video assets may be formatted differently relative to metadata associated with another group of video assets. For example, application server 215 and/or IMG server 220 may format metadata, associated with video assets in a particular group to be visually emphasized (e.g., brighter, larger size, a more conspicuous location, etc.) relative to metadata for video assets in another group. Thus, storefront 125 may visually distinguish metadata based on their associated groups.

Additionally, or alternatively, the selected metadata may be formatted based on a transaction history included in the profile. For example, application server 215 and/or IMG server 220 may format the metadata for video assets identified in the transaction history (e.g., video assets that were previously purchased, rented, and/or subscribed to) differently relative to other metadata that the user has not purchased, rented, and/or subscribed to. Application server 215 and/or IMG server 220 may format metadata based on a type of transaction indicated in the transaction history, such as formatting metadata associated with purchased video assets according to the first format and formatting metadata associated with rented video assets in a second format.

Application server 215 and/or IMG server 220, when formatting the metadata, may filter the metadata based on the identified device type associated with the user device 110. In certain implementations, application server 215 and/or IMG server 220 may additionally filter the selected metadata according to the information in the profile for the user. For example, the profile may include customer preferences that specify not initially presenting certain types of metadata associated with large file sizes (e.g., image metadata, etc.) to a type of user device 110 (e.g., a wireless device) due to bandwidth limitations on an associated service provider network or not initially presenting certain types of metadata related to a user's transaction history (e.g., metadata related to prior purchases, rentals, and/or subscriptions) to a type of user device 110 that is associated with a non-secure service provider network 140.

While FIG. 6 shows a flowchart diagram of an example process 600 for forming a storefront in connection with a video provisioning system, in other implementations, process 600 may include fewer blocks, different blocks, differently arranged blocks, or additional blocks than depicted in FIG. 6.

Figure 7:
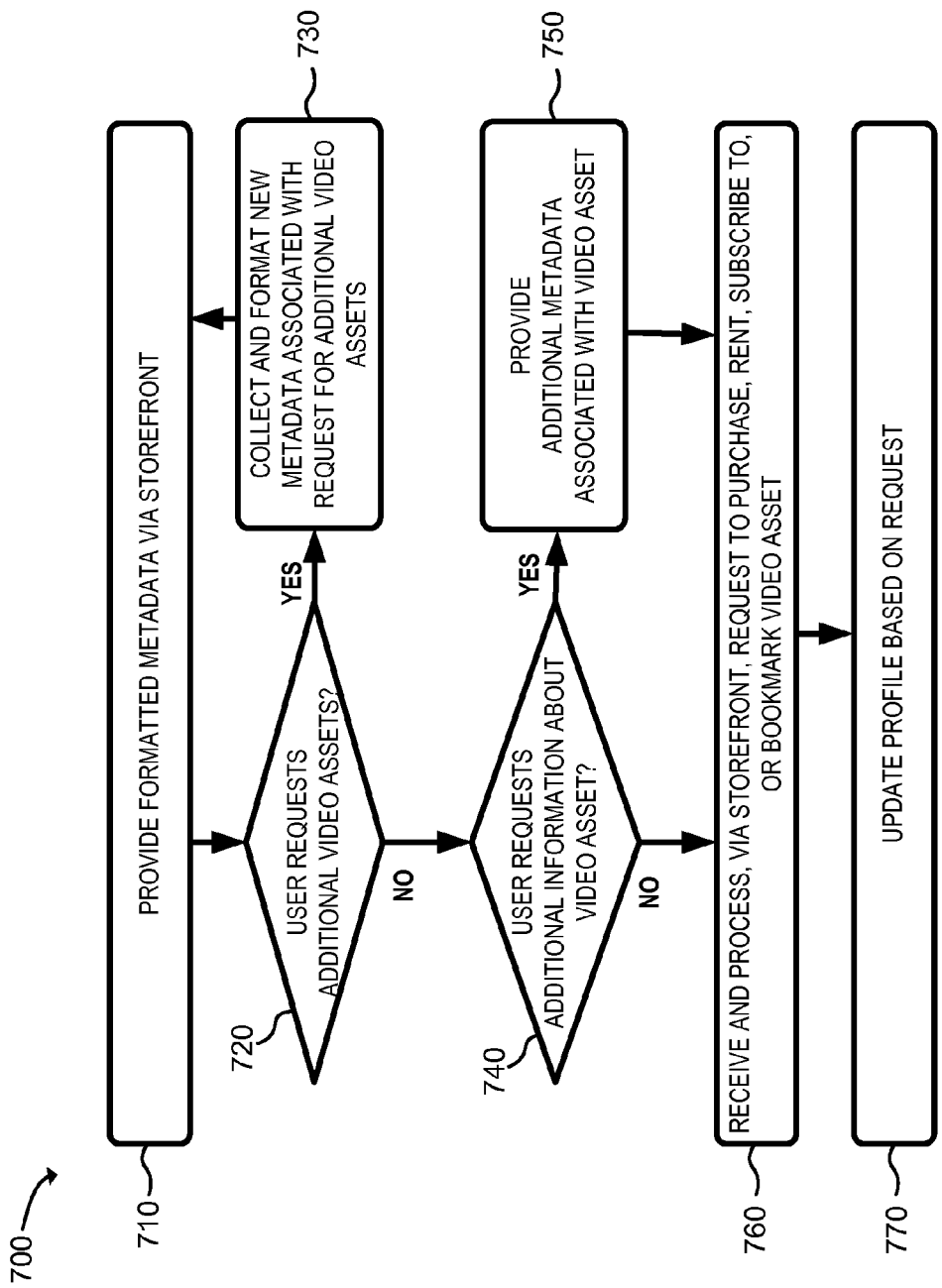
FIG. 7 is flowchart diagrams of an example process for providing a storefront within the environment of FIG. 1.

FIG. 7 is a flowchart diagram of an example process 700 for providing a storefront to a user device in connection with a video provisioning system. In one example implementation, process 700 may relate to providing storefront 125 to user device 110 and may be performed by application server 215 and/or IMG server 220, depending on a specific type of user device 110 receiving storefront 125. In another example implementation, some or all of process 700 may be performed by a device, or collection of devices separate from, or in combination with application server 215 and/or IMG server 220.

Process 700 may include providing formatted metadata via a storefront (block 710). For example, application server 215 and/or IMG server 220 may forward, via storefront 125, formatted metadata to user device 110. Application server 215 and/or IMG server 220 may collect and format the metadata in accordance with process 600.

Application server 215 and/or IMG server 220 may present the formatted metadata in the form of a top-level interface. As used herein, a top-level interface may include formatted metadata related to multiple video assets, such as video assets associated with a group.

The top-level interface may initially include formatted metadata that relates to video assets associated with a default group. As previously described with respect to process 600, the default group may be based on information in a profile for the user, such as stored user preferences and/or a transaction history. Additionally, or alternatively, the default group may be selected based on other criteria, such as service provider network 140 associated with user device 110.

Process 700 may further include determining whether a user requests additional video assets (block 720). For example, application server 215 and/or IMG server 220 may receive, via storefront 125, a request from user device 110 for information related to additional video assets. The request may relate to additional video assets associated with a currently displayed group of video assets. For example, the request may relate to viewing additional video assets included in the currently displayed group.

The request for addition video assets may also relate to changing a group of video assets displayed via storefront 125. For example, application server 215 and/or IMG server 220 may identify, via storefront 125, one or more additional available groups of video assets, and may receive information associated with a selection, by a user of one of the additional groups of video assets. Alternatively, or additionally, application server 215 and/or IMG server 220 may determine to change the group based on other criteria (e.g., when a user selection of a video asset is not received within a particular duration of time, no video assets are associated with currently selected group, etc.).

The request for addition video assets may also be related to a user-specified criteria for searching video assets. For example, the user, via storefront 125, may specify a search query for selecting video assets.

Process 700 may also include, when the user requests additional video assets (block 720—Yes), collecting and formatting new metadata associated with the request for additional video assets (block 730). For example, application server 215 and/or IMG server 220 may collect metadata associated with additional video assets associated with a request for additional video assets received from user device 110.

Application server 215 and/or IMG server 220 may collect metadata based on information in the profile for user device 110, in accordance with process 600. For example, the metadata associated with the requested additional video assets may be selected and formatted according a device type associated with user device 110, may include only a particular number of video assets, etc.

Process 700 may include determining whether a user requests additional information about a video asset (block 740). For example, application server 215 and/or IMG server 220 may receive, from user device 110, a request for additional information about a video asset. For example, application server 215 and/or IMG server 220 may present, via the top-level interface, formatted metadata related to multiple video assets (e.g., video assets in a group), and the request may relate to further information about one of the multiple video assets.

Process 700 may further include, when the user requests additional information about a video asset (block 740—Yes), providing additional metadata associated with the video asset (block 750). For example, application server 215 and/or IMG server 220 may collect metadata relating to the requested video asset and provide the additional metadata via the storefront 125. The collected metadata may include one or more of the metadata types stored in data structure 400. Application server 215 and/or IMG server 220 may retrieve the additional metadata, for example, from an associated memory, catalog server 235, VOD server 225, and/or from another source.

Application server 215 and/or IMG server 220 may select and format metadata based on information in the profile for user device 110, in accordance with process 600. For example, application server 215 and/or IMG server 220 may select metadata that is compatible with a device type associated with user device 110 and/or according to user preferences included in the profile.

In certain implementations, application server 215 and/or IMG server 220 may present the additional metadata via an asset-specific interface in the storefront 125. As used herein, the asset-specific interface may include formatted metadata associated with a particular video asset. Application server 215 and/or IMG server 220 may include, in the asset-specific interface, one or more additional types of metadata, associated with a particular video asset, that are not included in the top-level interface. Application server 215 and/or IMG server 220 may format the asset-specific interface based on the device type of user device 110 and/or information in the profile for device 110.

The additional metadata related to the specific video asset may further include metadata identifying another video asset. For example, application server 215 and/or IMG server 220 may recommend another video asset based on similarities in the metadata of the two video assets and/or based on information in the profile (e.g., the user's preferences, the transaction history associated with the user and/or user device 110, etc.).

Process 700 may further include receiving and processing, via the storefront, a request to purchase, rent, subscribe to, or bookmark a video asset (block 760). For example, application server 215 and/or IMG server 220 may receive, via storefront 125, information identifying a particular video asset and a requested action. As used herein, a purchase may include permanent access to the video asset; a rental may include temporary access to the video asset; a subscription may include a future access to the video asset; and a bookmark may include updating the profile to include a reference to the video asset.

When the request relates to delivery of the video asset to user device 110 (e.g., purchasing, renting, and/or subscribing to a video asset), application server 215 and/or IMG server 220 may identify a network location associated with access, by user device 110, to the video asset (e.g., a URL). For example, when the received request relates to purchasing, renting, and/or subscribing to a VOD video asset, application server 215 and/or IMG server 220 may forward, to user device 110, a location of the video asset associated with VOD server 225. Similarly, when the request received in block 760 relates to purchasing, renting, and/or subscribing to a CDN video asset, application server 215 and/or IMG server 220 may forward, to user device 110, a location of the video asset associated with CDN server 230.

The location of the video asset may be based on, for example, the profile for the user. For example, the location of the video asset may be associated with a media and/or delivery format that is compatible with user device 110 and is allowed based on the user's account status. When the request from one user device 110 relates to delivery of the video asset to another user device 110, application server 215 and/or IMG server 220 may identify the location of the video asset based on, for example, the profile associated with the other user device 110. For example, when a profile indicates that user device 110 (or another user device 110 associated with a common user) has already received a portion of the video asset, the location of the video asset may be associated with receiving an undelivered portion of the video asset.

Process 700 may include updating the profile based on the request (block 770). For example, application server 215 and/or IMG server 220 may update the profile for the user to include information related to the specific video asset and the type of request. For example, application server 215 and/or IMG server 220 may update the transaction history stored in the profile. Additionally, or alternatively, application server 215 and/or IMG server 220 may further update the profile to indicate a status of the request. For example, the updated information in the profile may indicate whether a video asset has been completely delivered to user device 110 or whether the video asset is available for viewing via another user device 110.

While FIG. 7 shows a flowchart diagram of example process 700 for providing a storefront to a user device in connection with a video provisioning system, in other implementations, process 700 may include fewer blocks, different blocks, differently arranged blocks, or additional blocks than depicted in FIG. 7.

Figure 8:
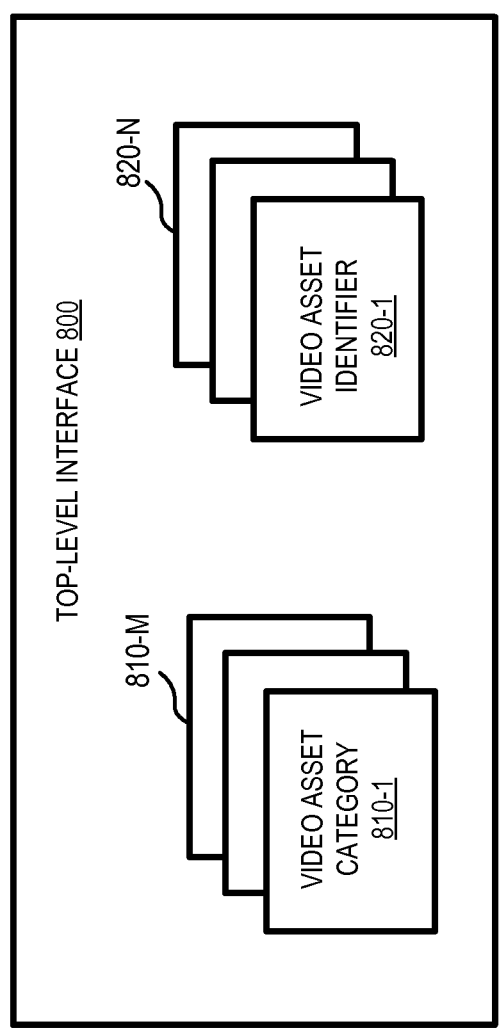
FIGS. 8 and 9 are schematic depictions of an example storefront according to an implementation described herein.

FIG. 8 shows a schematic diagram of an example top-level interface 800 associated with storefront 125. Top-level interface 800 may include one or more video asset groups 810-1, . . . , 810-M (where M≥1) (hereinafter referred to collectively as "video asset groups 810" and individually as "video asset group 810"); and one or more video asset identifiers 820-1, . . . , 820-N (where N≥1) (hereinafter referred to collectively as "video asset identifiers 820" and individually as "video asset identifier 820"). The information in top-level interface 800, shown in FIG. 8, are provided for explanatory purposes only, and in practice, top-level interface 800 may include additional, fewer, or different information than shown in FIG. 8.

Top-level interface 800 may concurrently display one or more video asset identifiers 820 associated with one of the video asset groups 810, such as a default video asset group 810. Thus, top-level interface 800 may present video asset identifier 820 for a video asset associated with the selected video asset group 810.

Video asset group 810 may associate one or more video asset identifiers 820 that share one or more types of metadata.

For example, video assets having metadata with a particular value for category field 445 may be associated with a particular video asset group 810. Video asset group 810 may also be based on one or more other metadata fields described above with respect to data structure 400 shown in FIG. 4. For example, video asset group 810 may include video assets that share metadata in title field 410 (e.g., video assets that contain a contain a common character string in their titles), genre field 415 (e.g., video assets in a particular genre), description field 420 (e.g., video assets that contain a contain a common character string in their descriptions), cast information field 425 (e.g., video assets associated with a particular actor), rating field 430 (e.g., video assets receiving a particular rating), and/or review field 450 (e.g., video assets receiving a particular review). Video asset group 810 may include video assets that share similar metadata in price field 435 (e.g., video assets available within a particular range of prices) and/or bundle field 460 (e.g., video assets available in a bundle). Video asset group 810 may include video assets that share metadata in format field 440 (e.g., video assets available in HD).

Additionally, or alternatively, video asset group 810 may associate a group of video assets based on information in a profile for the user. For example, application server 215 and/or IMG server 220 may define video asset group 810 based on a device type associated with user device 110 and/or a transaction history in the profile. For example, video asset group 810 may associated one or more video assets that were previously purchased, rented, subscribed to, and/or bookmarked by a user associated with user device 110.

Top-level interface 800 may further include a particular number and orientation of video asset groups 810 based on the profile for user device 110. For example, top-level interface 800 may concurrently display a number of asset categories 810, and this number may vary depending on a device type associated with user device 110.

Top-level interface 800 may visually emphasize, relative to another video asset group 810, a particular video asset group 810 associated with currently displayed video assets identifiers 820. For example, the particular video asset group 810 may be positioned at a more prominent position, have a more prominent appearance (e.g., larger, brighter, and/or distinctive lettering), etc.

Video asset identifier 820 may include information to identify an associated video asset. Video asset identifier 820 may include, for example, an identifier for a video asset (from asset ID field 405 in data structure 400), a title for the video asset (from title field 410 in data structure 400), and/or an image associated with the video asset (from cover art field 455 in data structure 400).

Figure 9:
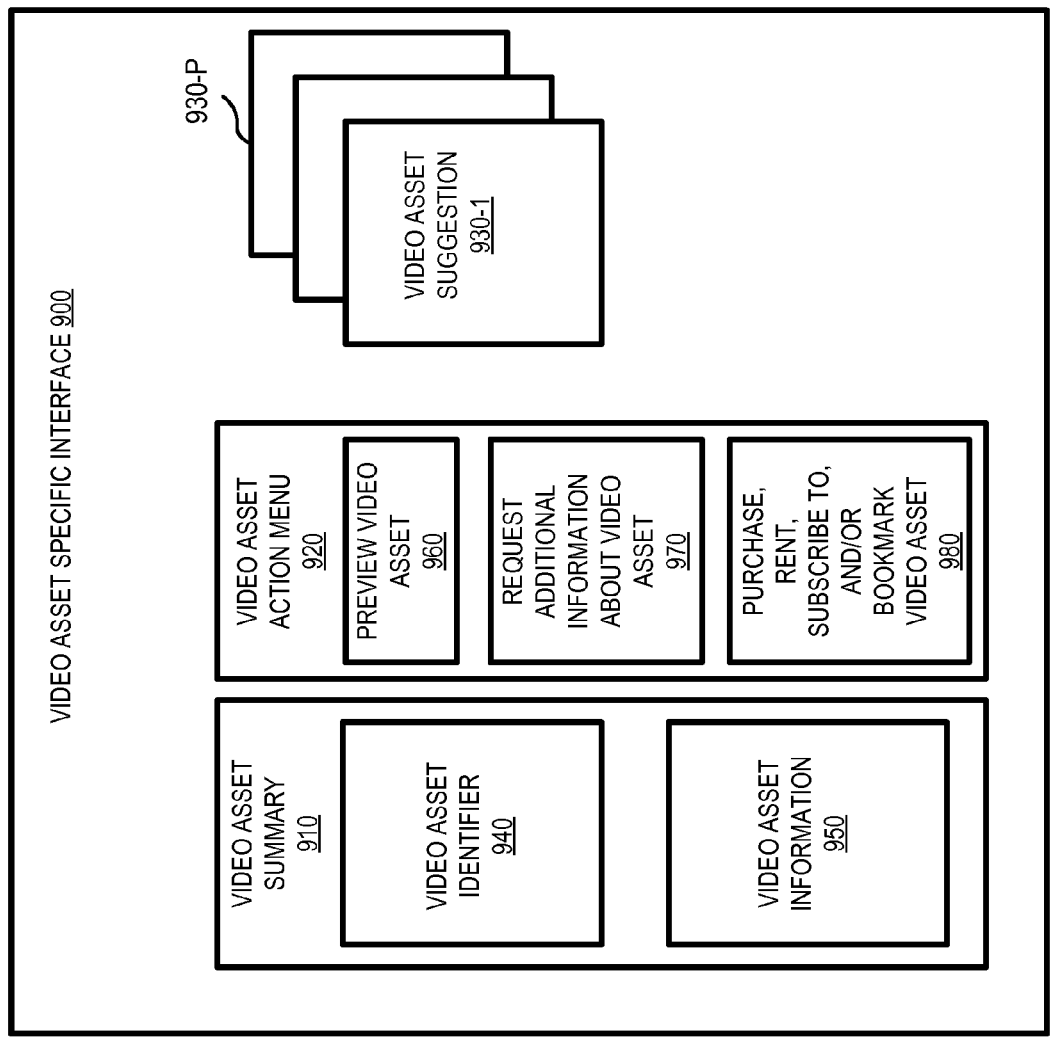

FIG. 9 is a schematic diagram of an example asset-specific interface 900 associated with storefront 125. Asset-specific interface 900 may include formatted metadata associated with a particular video asset. For example, asset-specific interface 900 may include video asset summary 910 that includes information related to contents of the video asset; video asset action menu 920 identifying one or more actions, for the particular video asset, that are available to user device 110 via storefront 125; and one or more related video asset suggestions 930-1, . . . , 930-P (where P≥1) (hereinafter referred to collectively as "related video asset suggestions 930" and individually as "related video asset suggestion 930") that identify other video assets that share one or more characteristics with the particular video asset. The information in asset-specific interface 900, shown in FIG. 9, are provided for explanatory purposes only, and in practice, asset-specific interface 900 may include additional, fewer, or different types of information than shown in FIG. 9.

Video asset summary 910, in asset-specific interface 900, may include, for example, video asset identifier 940. Video asset identifier 940 may provide identifying information for a particular video asset and may correspond, for example, to video asset identifier 820 included in top-level interface 800. For example, video asset identifier may include a title of the video asset (from title field 410 of data structure 400) and/or an image associated with the video asset (from cover art field 455 of data structure 400).

Video asset summary 910, in asset-specific interface 900, may also include video asset information 950 that includes additional information about the video asset, that is not already included in video asset identifier 940. Video asset information 950 may include, for example, a genre of a video asset (from genre field 615 in data structure 400), a description of the video asset (from description field 420 in data structure 400), cast members of the video asset (from cast information field 425 in data structure 400), an MPAA rating for the video asset (from rating field 430 in data structure 400)), and/or review information for the video asset (from review field 450 in data structure 400). Video asset information 950 may further include, for example, information related to pricing information for the video asset (from price field 435 in data structure 400), available formats for the video asset (from format field 440 in data structure 400), and/or available bundle information for the video asset (from bundle field 460 in data structure 400).

Video asset action menu 920, in asset-specific interface 900, may include, for example, a preview video asset option 960 to preview the particular video asset. In response to detecting a selection, by user device 110, of preview video asset option 960, storefront 125 may provide user device 110 with access to a preview of the video asset (e.g., a trailer). For example, storefront 125 may provide user device 110 with a location (e.g., a URL) for the preview. The preview may be a VOD preview (e.g., the preview is streamed to user device 110) or may be a CDN preview (e.g., user device downloads the preview). A preview provided through preview video asset option 960 may also depend on the profile for the user. For example, storefront 125 may provide a particular preview that is compatible with a device type associated with user device 110.

Video asset action menu 920, in asset-specific interface 900, may further include an request addition information about the particular video asset option 970. In response to detecting a selection, by user device 110, of request addition information about the particular video asset option 970, storefront 125 may provide user device 110 with additional information about the video asset. For example, storefront 125 collect and format additional metadata about the video asset and may update video asset information 950 to include the additional metadata. Request addition information about the particular video asset option 970 may further enable user device 110 to specify a type of additional information.

Video asset action menu 920, in asset-specific interface 900, may further include one or more options 980 to purchase, rent, subscribe to, and/or bookmark the particular video asset. In response to detecting a selection, by user device 110, of an option to bookmark the video asset, storefront 125 may modify a profile associated with user device 110 to include a reference to the video asset. In response to detecting a selection, by user device 110, of an option to purchase, rent, or subscribe to a video asset, storefront 125 may provide user device 110 with appropriate access to the video asset. For example, storefront 125 may identify a location (e.g., URL) to access a version of the video asset that is compatible with user device 110.

Asset-specific interface 900 may further include one or more related video asset suggestions 930. Video asset suggestions 930 may identify one or more other video assets that share one or more characteristics with the particular video asset identified by asset-specific interface 900. The video assets, in video asset suggestions 930, may be selected, for example, based on a comparison of the metadata of the particular video asset with metadata of other video assets stored by catalog server 235. For example, video asset suggestion 930 may identify a video asset in a common genre, with a common actor, having a common rating, available in a similar format, available at a particular price, etc.

Additionally, or alternatively, video asset suggestion 930 may suggest another video asset based on information in a profile for the user. For example, video asset suggestion 930 may identify a video asset that shares metadata with video asset identified in transaction history for user device 110. Video asset suggestion 930 may also identify a video asset that relates to a topic of interest to the user that is identified in the profile.

Figure 10:
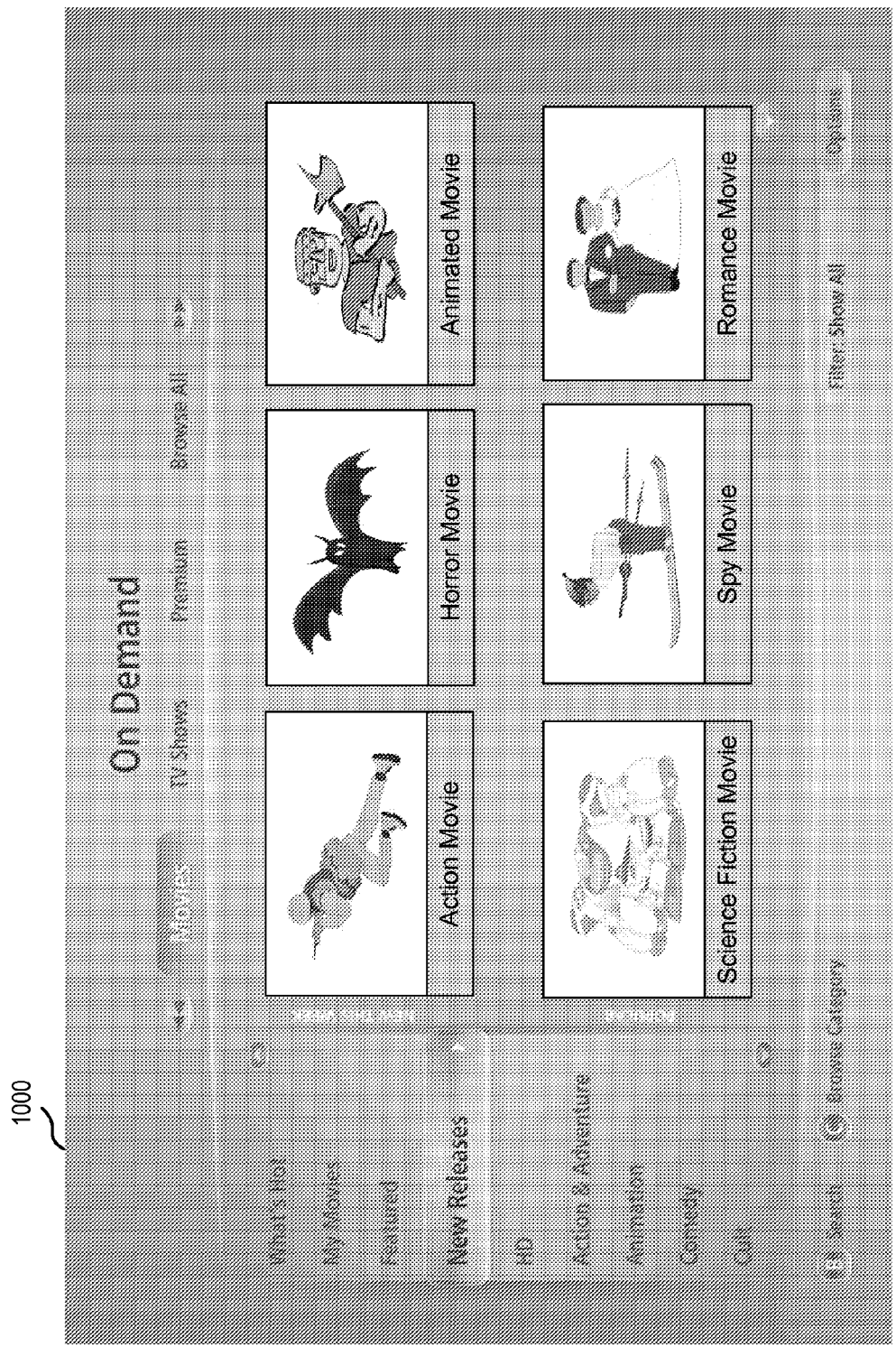
FIGS. 10-13, 14A, 14B, and 15 are example screenshots that may be provided by a storefront according to an implementation described.

FIG. 10 shows an example top-level interface ("STB top-level interface 1000") that may be provided through a STB user device 110. STB top-level interface 1000 may be provided to an STB user device 110 in connection with IMG server 220. Thus, STB top-level interface 1000 may be formatted by IMG server 220 for presentation by the STB user device 110.

STB top-level interface 1000 may initially display video assets associated with a default group. As shown in FIG. 10, STB top-level interface 1000 may display identifiers (e.g., titles and/or images) associated with video assets in the category of "Movies" in "New Releases" group (e.g., movies that have become recently available).

STB top-level interface 1000 may show other available categories of video assets (e.g., "TV Shows," "Premium" channels, or a combination of these categories ("Browse All")). As further shown in FIG. 10, STB top-level interface 1000 may also identify, for each of the categories, groups of popular ("What's Hot") or featured ("Featured") video assets. STB top-level interface 1000 may also identify, for each of the categories, a group of video assets related to a particular format (e.g., high definition (HD)) or a particular genre (e.g., "Action and Adventure," "Animation," "Comedy," or "Cult"). STB top-level interface 1000 may also present a group of bookmarked video assets ("My Movies"). In response to receiving a selection of one of the groups and/or categories of video assets, STB top-level interface 1000 may display metadata associated with video assets associated with the selected group and/or category.

The information in STB top-level interface 1000, shown in FIG. 10, are provided for explanatory purposes only, and in practice, STB top-level interface 1000 may include additional, fewer, or different types of information than shown in FIG. 10.

Figure 11:
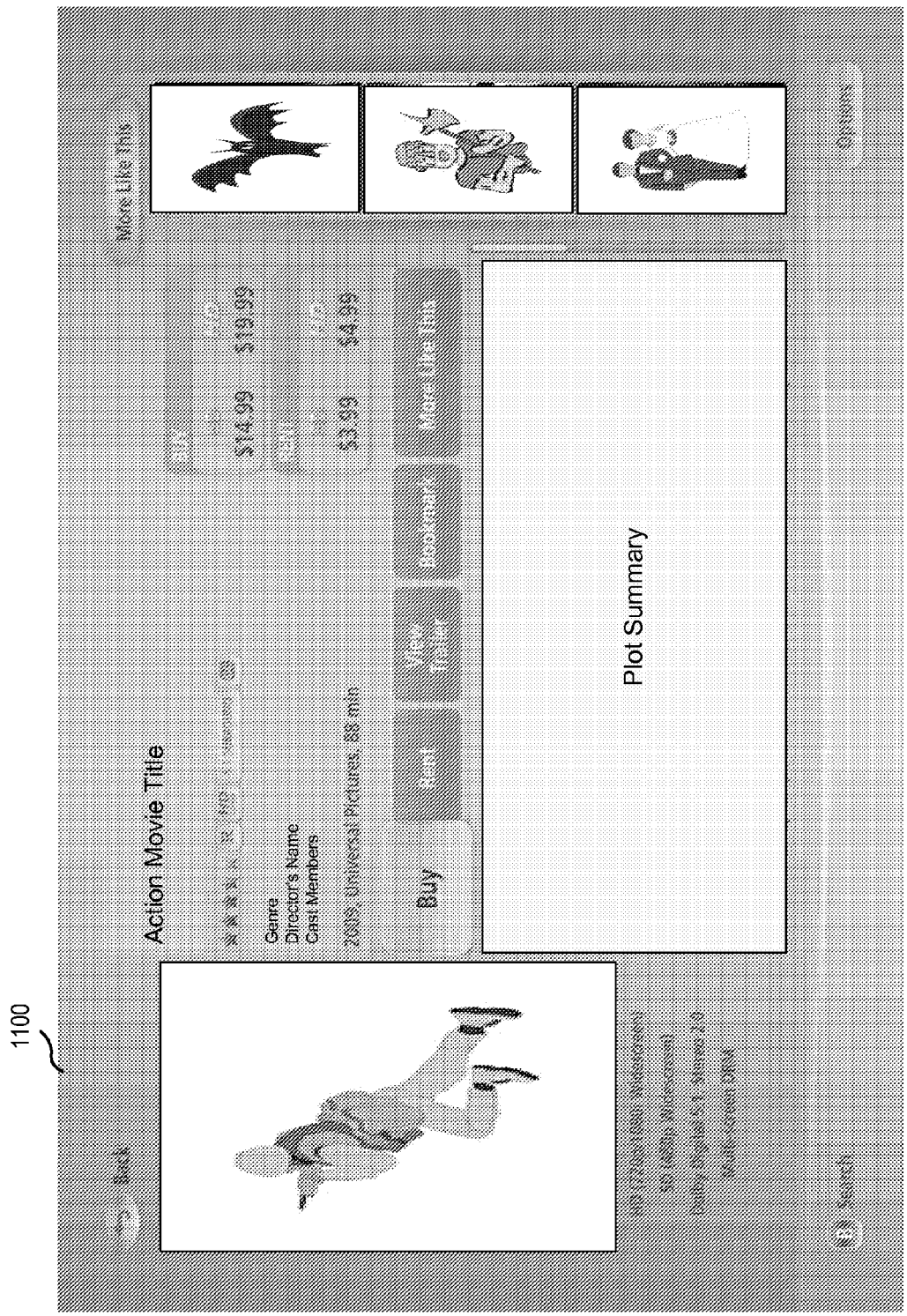

FIG. 11 shows an example asset-specific interface ("STB asset-specific interface 1100") that may be provided through a STB user device 110 in response to a user selection of a particular video asset via STB top-level interface 1000. STB asset-specific interface 1100 may be provided to STB user device 110 in connection with IMG server 220 and may be formatted for presentation by the STB user device 110.

STB asset-specific interface 1100 may include information about the video asset, such as a title, an associated image, a review, a rating, a genre, a director's name, cast members, a plot summary, duration, compatible audio formats, etc. STB asset-specific interface 1100 may also present information identifying available format options (e.g., HD and SD), available transaction options (e.g., buying or renting the video asset), and pricing information related to the format and transaction options for the video asset. STB asset-specific interface 1100 may further include action options related to the video asset, such as "Buy," "Rent," "View Trailer," and "Bookmark." STB asset-specific interface 1100 may further include a "More Like This" section that identifies other video assets related to the video asset identified by STB asset-specific interface 1100.

The information in STB asset-specific interface 1100, shown in FIG. 11, is provided for explanatory purposes only, and in practice, STB asset-specific interface 1100 may include additional, fewer, or different types of information than shown in FIG. 11. For example, STB asset-specific interface 1100 may further include information regarding compatibility of the video asset with other (i.e., non-STB) user devices 110.

Figure 12:
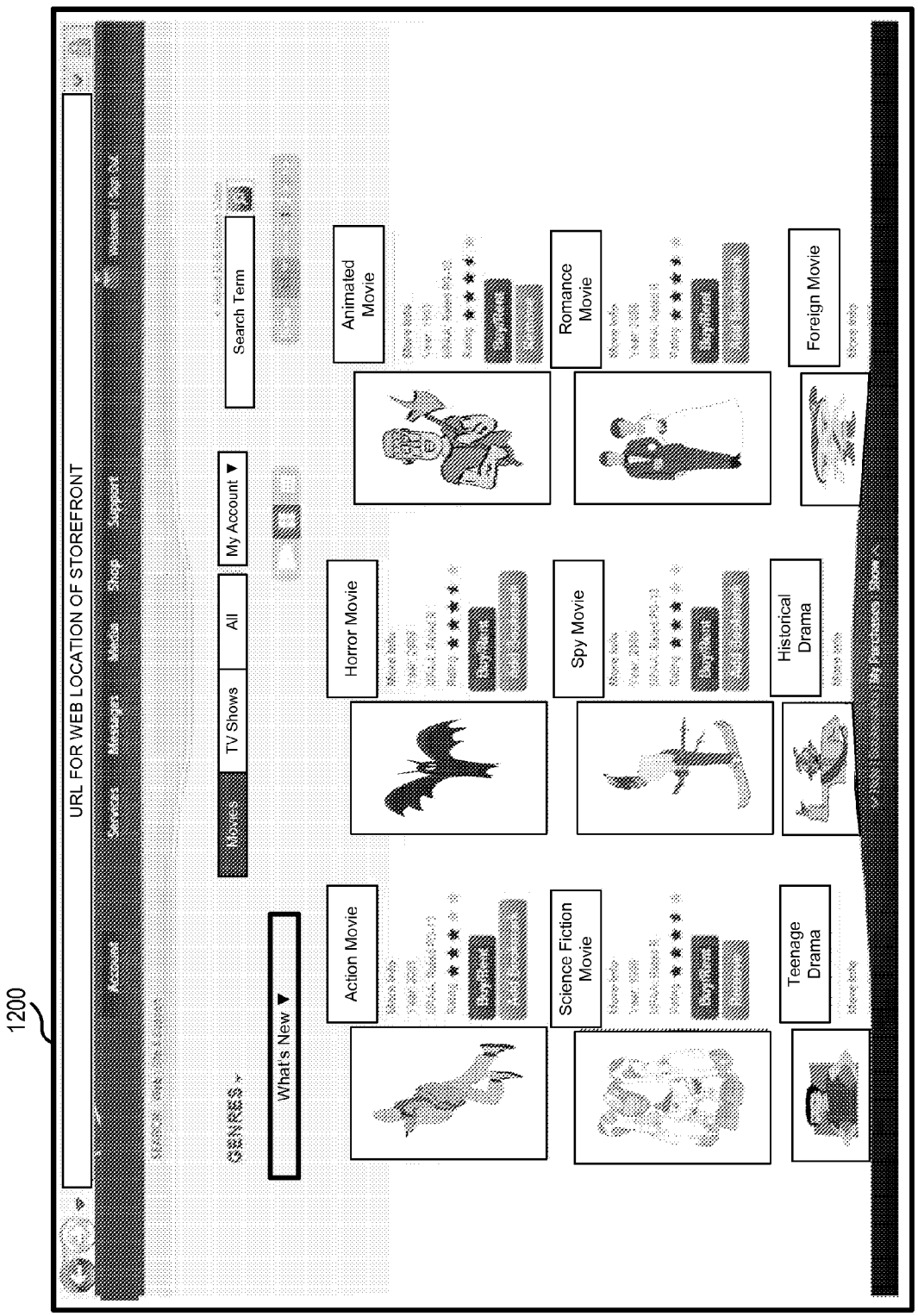

FIG. 12 shows an example top-level interface ("web-based top-level interface 1200") that may be provided through a non-STB user device 110, such as a computer device. Web-based top-level interface 1200 may be provided to user device 110 via application server 215. Thus, application server 215 may format web-based top-level interface 1200 for presentation via the non-STB user device 110. For example, web-based top-level interface 1200 may be formatted for access through a client-side browser application, such as Microsoft® Internet Explorer or Google® Chrome, operating on the non-STB user device 110.

Web-based top-level interface 1200 may initially display video assets associated with a default group (e.g., "What's New") in a default category (e.g., "Movies"). A default group presented via web-based top-level interface 1200 may correspond to a default group presented via STB top-level interface 1000. Thus, video assets initially identified on web-based top-level interface 1200 may correspond to video assets initially identified on STB top-level interface 1000. In this way, a user may be presented with the same group of video assets, regardless the user device used to view the storefront 125.

Web-based top-level interface 1200 may display identifiers (e.g., titles and images) and additional metadata (e.g., "Year," "MPAA" rating, and "Rating") and action options (e.g., "Buy/Rent" and "Add Bookmark") associated with video assets in the specified group. Web-based top-level interface 1200 may further identify different categories of video assets (e.g., "TV Shows," "All," etc.). Web-based top-level interface 1200 may further include a drop down menu that may enable a user to select a different group, or "Genres" within a category of video assets. Web-based top-level interface 1200 may further include an input search field to accept a search term for identifying a matching video asset.

Figure 13:
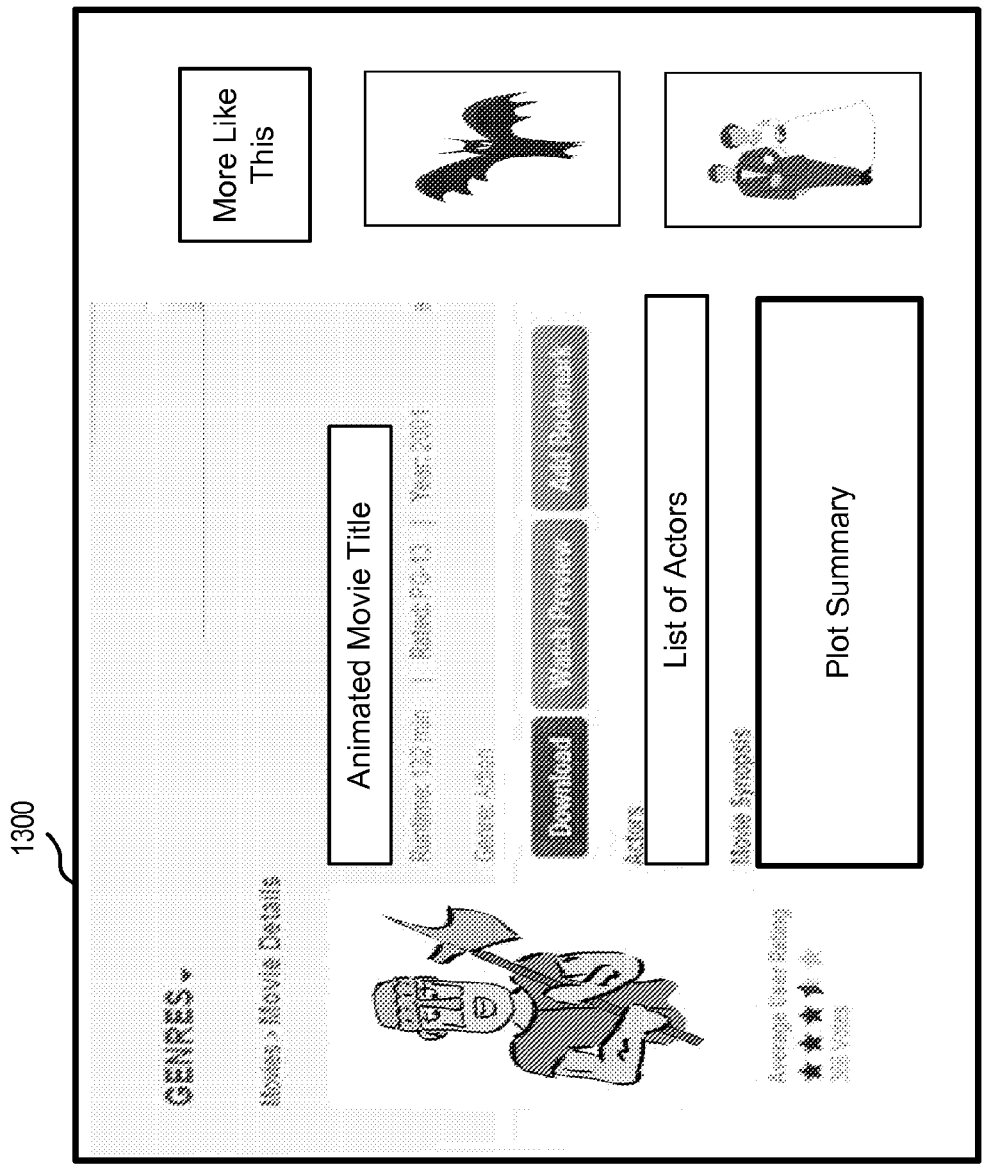

FIG. 13 shows an example asset-specific interface ("web-based asset-specific interface 1300") that may be provided to a non-STB user device 110 in response to a user selection of a particular video asset via web-based top-level interface 1200. Web-based asset-specific interface 1300 may be provided to user device 110 in connection with application server 215. Application server 215 may format web-based asset-specific interface 1300 for presentation by the non-STB user device 110, such as via a browser application.

Web-based asset-specific interface 1300 may include metadata information about the particular video asset, such as a title, a runtime, a rating, a genre, a user rating, etc. Web-based asset-specific interface 1300 may also include action options related to the video asset, such as "Download," "WatchPreview," and "Bookmark." Web-based asset-specific interface 1300 may further include a "More Like This" section that identifies other video assets related to the particular video asset specified by web-based asset-specific interface 1300.

The information in web-based asset-specific interface 1300, shown in FIG. 13, is provided for explanatory purposes only, and in practice, web-based asset-specific interface 1300 may include additional, fewer, or different types of information than shown in FIG. 13. For example, web-based asset-specific interface 1300 may further include, for example, information regarding compatibility of the particular video asset with other user devices 110 associated with the user, such as an STB user device 110.

Figure 14B:
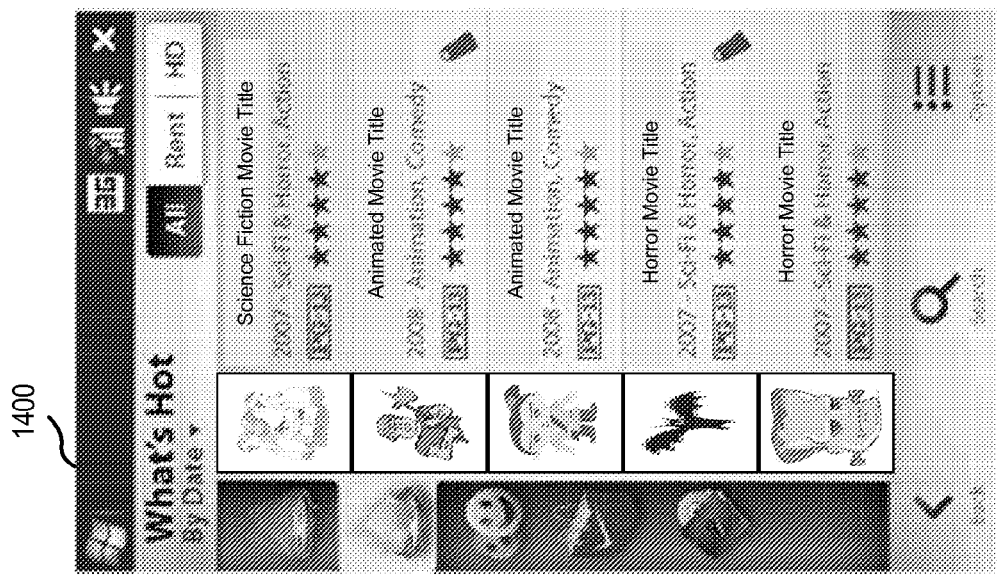
Figure 14A:
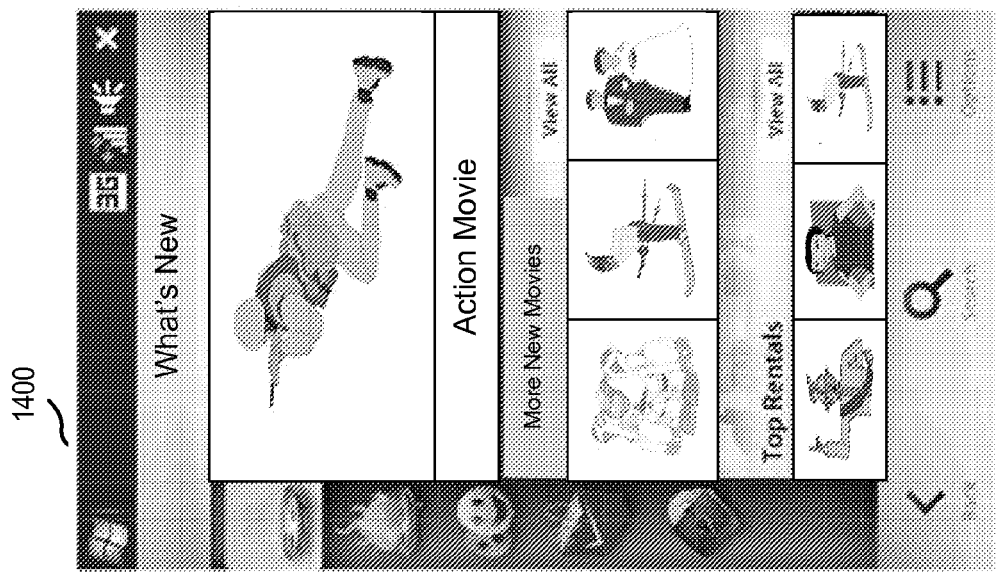

FIGS. 14A and 14B show an example top-level interface ("application-based top-level interface 1400") that may be provided through a non-STB user device 110, such as a mobile handheld device. Application-based top-level interface 1400 may be provided to user device 110 via application server 215. Application-based top-level interface 1400 may be presented by an application, resident on user device 110, may acquire and present formatted metadata from application server 215.

As shown in FIG. 14A, application-based top-level interface 1400 may identify video assets associated with one or more group, such as "Featured," "What's New," "Top Rentals." Application-based top-level interface 1400 may initially display video assets associated with a default group (e.g., "What's New"). A default group initially presented via application-based top-level interface 1400 may correspond to a default group specified by STB top-level interface 1000 and/or web-based top-level interface 1200. Thus, one or more of the video assets, presented via application-based top-level interface 1400, may correspond to video assets presented via STB top-level interface 1000 and/or web-based top-level interface 1200. In this way, a user may be presented with the same group of video assets, regarding the user device used to view the storefront 125.

As shown in FIG. 14B, application-based top-level interface 1400 may present different video assets in response to a user selection of a different group (e.g., a "What's Hot" group, that may relate to prior purchases, rentals, and/or subscriptions across all user devices 110 accessing VPS 120). As further shown in FIG. 14B, application-based top-level interface 1400 may enable a user to filter video assets in the "What's Hot" group based on a time period associated with the purchases, rentals, and/or subscriptions ("By Date"). As further shown in FIG. 14B, application-based top-level interface 1400 may further enable a user to filter video assets in group based on a desired transaction type (e.g., "What's Hot" video assets for "Rent") or a format option (e.g., "What's Hot" video assets in "HD").

The information included in application-based top-level interface 1400, shown in FIGS. 14A and 14B, is provided for explanatory purposes only, and in practice, application-based asset-specific interface 1400 may include additional, fewer, or different types of information than shown in FIG. 14.

Figure 15:
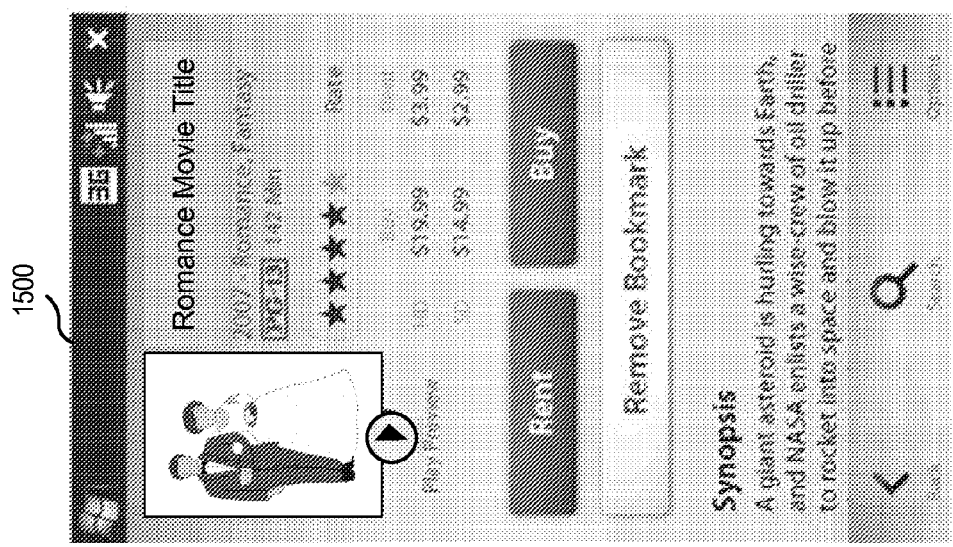

FIG. 15 shows an example application-based asset-specific interface 1500 that may be provided through non-STB user device 110. Application-based asset-specific interface 1500 may be provided to user device 110 via application server 215. Application server 215 may format application-based asset-specific interface 1500 for presentation by the non-STB user device 110 via an application residing on user device 110.

Application-based asset-specific interface 1500 may be activated upon bookmarking or another selection of a particular video asset listed in application-based top-level interface 1400. Application-based asset-specific interface 1500 may include various metadata related to the selected video asset. Application-based asset-specific interface 1500 may further include information regarding the pricing of different actions available to user device 110 (e.g., "Rent" or "Buy") related to different versions of content of the video asset (e.g., "SD" or "HD"). Application-based asset-specific interface 1500 may further include an option to remove a bookmark associated with the specific video asset.

Systems and/or methods described herein may enable a storefront to collect metadata associated with a video assets and to format the metadata for presentation on different types of user devices. The storefront may further include a graphical user interface to present the metadata through various types of user devices, associated with a user, over various types of networks. The graphical user interface in the storefront may further enable a user, through any of the various types of user devices, to request additional information about the video asset and perform transactions related to the videos asset.

The foregoing description provides illustration and description, but is not intended to be exhaustive or to limit the implementations to the precise form disclosed. Modifications and variations are possible in light of the above teachings or may be acquired from practice of the embodiments.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed:

1. A method comprising:
   registering, by a server device, a plurality of types of user devices;
   receiving, by the server device, metadata associated with two or more video assets;
   generating, by the server device and based on the metadata, first formatted metadata of the two or more video assets,
      the first formatted metadata being formatted to be compatible with a first type of user device, of the plurality of types of user devices, that corresponds to a set top box;
   providing, by the server device and via a storefront, the first formatted metadata to the first type of user device;
   generating, by the server device and based on the metadata, second formatted metadata of the two or more video assets,
      the second formatted metadata being formatted to be compatible with a second type of user device, of the plurality of types of user devices, that is a different type of device than the set top box;
   providing, by the server device and via the storefront, the second formatted metadata to the second type of user device;
   receiving, by the server device and from a user device of the plurality of types of user devices, a request to bookmark a video asset of the two or more video assets;
   obtaining, by the server device, a profile associated with the user device;
   updating, by the server device, the profile to include a reference to metadata associated with the video asset,
      the reference enabling the metadata associated with the video asset to be accessed within a period of time that is less than another period of time associated with accessing the metadata associated with the video asset via the storefront;
   receiving, by the server device, a request for the video asset from the user device;
   retrieving, by the server device, information associated with the profile,
      the information associated with the profile identifying a particular type of user device, of the plurality of types of user devices, associated with the user device; and
   transmitting, by the server device and to the user device, information identifying a uniform resource locator (URL) for obtaining a copy of the video asset that is formatted for the particular type of user device,
      the information identifying the URL including a reference to a video on-demand (VOD) network that enables streaming access to the video asset when the video asset is a VOD video asset, and
      the information identifying the URL including a reference to a content delivery network that enables non-streaming access to the video asset when the video asset is not the VOD video asset.

2. The method of claim 1, further comprising:
   receiving, from one of the first type of user device or the second type of user device, a selection of a particular video asset, of the two or more video assets; and
   providing, to the one of the first type of user device or the second type of user device, additional metadata associated with the particular video asset,
      where the additional metadata differs from the received metadata associated with the two or more video assets, and where the additional metadata is formatted for presentation on the one of the first type of user device or the second type of user device.

3. The method of claim 1, where the server device includes an application server and an interactive media guide (IMG) server,
where providing the first formatted metadata to the first type of user device includes providing the first formatted metadata through the IMG server, and
where providing the second formatted metadata to the second type of user device includes providing the second formatted metadata via the application server.

4. The method of claim 1, where the metadata includes one or more of:
a plurality of respective identifiers that correspond to the two or more video assets;
a plurality of respective prices associated with the two or more video assets;
a plurality of respective descriptions associated with the two or more video assets;
information associated with respective genres associated with the two or more video assets; or
information associated with respective ratings associated with the two or more video assets.

5. The method of claim 1, where the method further comprises:
accessing a first profile associated with the first type of user device,
where the first profile includes first configuration information for the first type of user device, and
accessing a second profile associated with the second type of user device,
where the second profile includes second configuration information for the second type of user device,
where generating the first formatted metadata of the two or more video assets is based on the first profile, and
where generating the second formatted metadata of the two or more video assets is based on the second profile.

6. The method of claim 5, where at least one of the first profile or the second profile further includes video asset selection criteria, and
where receiving the metadata associated with the two or more video assets further includes:
receiving metadata associated with a plurality of video assets that include the two or more video assets,
selecting, based on the video asset selection criteria, the two or more video assets, from the plurality of video assets, and
identifying the metadata associated with the two or more video assets.

7. The method of claim 1, where providing the first formatted metadata to the first type of user device further includes:
displaying the first formatted metadata via an interactive program guide that is accessible by the first type of user device, and
where providing the second formatted metadata to the second type of user device further includes:
displaying the second formatted metadata via a webpage that is accessible by the second type of user device.

8. A device comprising:
a memory to store metadata associated with a video asset; and
a processor to:
register two or more different types of user devices,
process the metadata to enable the video asset to be advertised to the two or more different types of user devices,
the two or more different types of user devices including a set top box type of user device and another type of user device that is a different type of device than the set top box type of user device,
the processor, when processing the metadata, being further to:
generate first formatted metadata, associated with the video asset, that is compatible with the set top box type of user device and is not compatible with the other type of user device, and
generate second formatted metadata, associated with the video asset, that is compatible with the other type of user device and is not compatible with the set top box type of user device,
transmit, via a storefront, the first formatted metadata to the set top box type of user device,
transmit, via the storefront, the second formatted metadata to the other type of user device,
receive, from a user device of the two or more different types of user devices, a request to bookmark the video asset,
retrieve a profile associated with the user device,
update the profile to include a reference to the video asset,
the reference enabling the user to access the video asset within a period of time that is less than another period of time associated with accessing the video asset via the storefront, receive, from the user device, a request for the video asset, retrieve information associated with the profile,
the information associated with the profile identifying a particular type of user device, of the two or more different types of user devices associated with the user device and
transmit, to the user device, information identifying a uniform resource locator (URL) that enables the user device to obtain a copy of the video asset that is formatted for the particular type of user device,
when the video asset is a video on-demand (VOD) video asset, the information identifying the URL including a first reference to a VOD network that enables streaming access to the VOD video asset, and
when the video asset is not the VOD video asset, the information identifying the URL including a second reference to a content delivery network that enables non-streaming access to the video asset.

9. The device of claim 8, where the memory is further to store metadata associated with a plurality of video assets, and where the processor is further to:
form, based on the metadata associated with the plurality of video assets, a listing that identifies the plurality of video assets,
send the listing to the two or more different types of user devices, and
receive, from at least one of two or more different types of user devices, a selection from the listing,
where the selection identifies the video asset, and
where the processor transmits the processed metadata, associated with the video asset, to at least one of the two or more different types of user devices based on receiving the selection.

10. The device of claim 9, where the processor, when forming the listing, is further to:
form a first listing that is compatible with the set top box type of user device and is not compatible with the other type of user device, and
form a second listing that is compatible with the other type of user device and is not compatible with the set top box type of user device, and
where the processor, when sending the listing, is further to:
send the first listing to the set top box type of user device, and
send the second listing to the other type of user device.

11. The device of claim 8, where the processor, when processing the metadata, is further to:
determine a video asset group that includes the video asset, and
indicate, via the first formatted metadata and the second formatted metadata, that the video asset is included in the video asset group.

12. The device of claim 8, where, when registering the two or more different types of user devices, the processor is to:
receive information indicating that the storefront is to be provided to the user device via a first network only when a second network is unavailable for providing the storefront to the user device.

13. The device of claim 8, where the processor is further to:
access a first profile associated with the set top box type of user device,
where the first profile includes first configuration information associated with the set top box type of user device; and
access a second profile associated with the other type of user device,
where the second profile includes second configuration information associated with the other type of user device,
where, when generating the first formatted metadata, the processor is to:
generate the first formatted metadata based on the first configuration information, and
where, when generating the second formatted metadata, the processor is to:
generate the second formatted metadata based on the second configuration information.

14. The device of claim 8, where the device includes at least one of an application server or an interactive media guide (IMG) server, and
where at least one of:
when, transmitting the first formatted metadata to the set top box type of user device, the processor is to transmit the first formatted metadata through the IMG server, or
when, transmitting the second formatted metadata to the other type of user device, the processor is to transmit the second formatted metadata via the application server.

15. A non-transitory computer-readable medium to store instructions, the instructions comprising:
one or more instructions that, when executed by a processor of a server device, cause the processor to:
register a plurality of user devices associated with a user,
the plurality of user devices including a first user device that is associated with a television service provider network and a second user device that is associated with a data service provider network,
the first user device being a different device type than the second user device;
form a storefront,
the one or more instructions to form the storefront including:
one or more instructions to format metadata, related to a video asset, in a first format associated with the first user device, and
one or more instructions to format the metadata, related to the video asset, in a second format associated with the second user device;
provide the storefront to the first user device and the second user device,
the one or more instructions to provide the storefront including:
one or more instructions to transmit the metadata, in the first format, to the first user device, and
one or more instructions to transmit the metadata, in the second format, to the second user device;
receive, from one of the first user device or the second user device, a request to bookmark the video asset;
obtain a profile associated with the one of the first user device or the second user device;
update the profile to include a reference to the video asset,
the reference enabling the video asset to be accessed within a period of time that is less than another period of time associated with accessing the video asset via the storefront;
receive, from the one of the first user device or the second user device, a request for the video asset;
retrieve information associated with the profile,
the information associated with the profile identifying a particular type of user device associated with the one of the first user device or the second user device; and
transmit, to the one of the first user device or the second user device, information identifying a uniform resource locator (URL) for obtaining a copy of the video asset that is formatted for the particular type of user device,
when the video asset is a video on-demand (VOD) video asset, the information identifying the URL including a first reference to a VOD network that enables streaming access to the VOD video asset, and
when the video asset is not the VOD video asset, the information identifying the URL including a second reference to a content delivery network that enables non-streaming access to the video asset.

16. The non-transitory computer-readable medium of claim 15, where the instructions further comprise:
one or more instructions to identify a first network location associated with a first copy of the video asset,
where the first copy is compatible with the first user device; and
one or more instructions to identify a second network location associated with a second copy of the video asset,
where the second copy is compatible with the second user device; and
where the one or more instructions to transmit the information identifying the URL include:
one or more instructions to send, when the request is received from the first user device, information identifying the first network location to the first user device; and
one or more instructions to send, when the request is received from the second user device, information identifying the second network location to the second user device.

17. The non-transitory computer-readable medium of claim 16, where the first network location is associated with streaming video associated with the video asset, and where the second network location is associated with non-streaming access to the video asset.

18. The non-transitory computer-readable medium of claim 15, where the video asset is one of a plurality of video assets, and
where the instructions further comprise:
one or more instructions to form a listing that identifies the plurality of video assets;
one or more instructions to transmit the listing to the first user device and to the second user device; and
one or more instructions to receive, from at least one of the first user device or the second user device, a selection of the video asset,
where the one or more instructions to transmit the metadata, in the first format, include:
one or more instructions to transmit the metadata, in the first format, to the first user device based on receiving the selection, and
where the one or more instructions to transmit the metadata, in the second format, include:
one or more instructions to transmit the metadata, in the second format, to the second user device based on receiving the selection.

19. The non-transitory computer-readable medium of claim 18, where the one or more instructions to form the listing further include:
one or more instructions to format the listing in the first format;
one or more instructions to format the listing in the second format;
one or more instructions to transmit the listing, in the first format, to the first user device; and
one or more instructions to transmit the listing, in the second format, to the second user device.

20. The non-transitory computer-readable medium of claim 15, where the instructions further include:
one or more instructions to access a first profile associated with the first user device,
where the first profile includes first configuration information for the first user device; and
one or more instructions to access a second profile associated with the second user device,
where the second profile includes second configuration information for the second user device,
where the one or more instructions to format the metadata in the first format include:
one or more instructions to format the metadata based on the first configuration information, and
where the one or more instructions to format the metadata in the second format include:
one or more instructions to format the metadata based on the second configuration information.

21. The non-transitory computer-readable medium of claim 15, where the instructions further include:
one or more instructions to access the profile associated with the one of the first user device or the second user device,
where the profile includes information associated with one or more user preferences;
one or more instructions to identify, based on the information associated with the one or more user preferences, a video asset group; and
one or more instructions to determine that the video asset is included in the identified video asset group,
where the one or more instructions to transmit the metadata, in the first format, include:
one or more instructions to transmit the metadata, in the first format, to the first user device based on determining that the video asset is included in the video asset group, and
where the one or more instructions to transmit the metadata, in the second format, include:
one or more instructions to transmit the metadata, in the second format, to the second user device based on determining that the video asset is included in the video asset group.

22. The non-transitory computer-readable medium of claim 21, where the information associated with the one or more user preferences includes at least one of:
an input, from a user, identifying the one or more user preferences,
data related to prior transactions associated with the user, or
data related to the bookmark.

23. The non-transitory computer-readable medium of claim 21, where the instructions further include:
one or more instructions to receive, from the one of the first user device or the second user device, a request for another video asset group that differs from the identified video asset group,
where the other video asset group does not include the video asset and includes another video asset;
one or more instructions to access metadata associated with the other video asset; and
one or more instruction to update the storefront to include:
an indication of the identified video asset group, and
the metadata associated with the other video asset.

24. The non-transitory computer-readable medium of claim 15, where the instructions further comprise:
one or more instructions to receive, from one of the first user device or the second user device, a request to receive additional information about the video asset;
one or more instructions to access additional metadata associated with the video asset; and
one or more instructions to update the storefront to include the additional metadata associated with the video asset.

* * * * *